US 8,383,115 B2

(12) United States Patent
Kaushik et al.

(10) Patent No.: US 8,383,115 B2
(45) Date of Patent: Feb. 26, 2013

(54) ENGINEERED SCFV AGAINST BOVINE HERPES VIRUS TYPE I

(75) Inventors: Azad Kumar Kaushik, Morriston (CA); Madhuri Koti, Guelph (CA); Eva Nagy, Guelph (CA)

(73) Assignee: Azad Kumar Kaushik, Morriston, Ontario (CA)

( * ) Notice: Subject to any disclaimer, the term of this patent is extended or adjusted under 35 U.S.C. 154(b) by 363 days.

(21) Appl. No.: 12/669,345

(22) PCT Filed: Jul. 18, 2008

(86) PCT No.: PCT/CA2008/001302
§ 371 (c)(1),
(2), (4) Date: Jan. 15, 2010

(87) PCT Pub. No.: WO2009/009892
PCT Pub. Date: Jan. 22, 2009

(65) Prior Publication Data
US 2010/0196375 A1    Aug. 5, 2010

Related U.S. Application Data

(60) Provisional application No. 60/950,638, filed on Jul. 19, 2007.

(51) Int. Cl.
A61K 39/42 (2006.01)
C12Q 1/04 (2006.01)
G01N 33/53 (2006.01)
C07K 16/08 (2006.01)

(52) U.S. Cl. ........ 424/135.1; 435/5; 435/7.1; 530/388.3

(58) Field of Classification Search .................. None
See application file for complete search history.

(56) References Cited

U.S. PATENT DOCUMENTS 4,946,778 A * 8/1990 Ladner et al. ................ 435/69.6
5,026,646 A   6/1991 Levings et al.
5,789,177 A * 8/1998 Rijsewijk et al. ............ 435/7.1

FOREIGN PATENT DOCUMENTS

WO    WO 98/21581    * 5/1998

OTHER PUBLICATIONS

Shen et al., Anal. Chem., 2005, 77:797-805.*
Raats et al., Journal of Immunoassay & Immunochemistry, 2003, 24(2):115-146.*
Casey et al., Protein Engineering, 2000, 13(6):445-452.*
Koti, M., et al., "Construction of single-chain Fv with two possible CDR3H conformations but similar inter-molecular forces that neutralize bovine herpesvirus 1." Molecular Immunology, 2010, pp. 953-960, vol. 47.
Saini, S.S., et al., "Structural Evidence for a New IgG1 Antibody Sequence Allele of Cattle", Scandinavian Journal of Immunology, 2007, pp. 32-38, vol. 65, No. 1.
Saini, S.S., et al., "A Single Predominantly Expressed Polymorphic Immuoglogulin V( sub H) Gene Family, Related to Mammalian Group, I, Clan, II, is Identified in Cattle", Molecular Immunology, 1997, pp. 641-651, vol. 34, No. 8-9.
Saini, S.S, et al., *Bos taurus* hybridoma S1-BL5C2.870005 antibovine herpes virus-1 IgG1 mRNA, V region, partial cds, GenBank sequence database Accession No. U36823, 1998.
Saini, S.S, et al., *Bos taurus* immunoglobin light chain variable region mRNA, partial cds, GenBank sequence database Accession No. AF015807, 2000.
Van Engelenburg, F. A., M. J. Kaashoek, et al (1994). "A glycoprotein E deletion mutant of bovine herpesvirus 1 is avirulent in calves." J Gen Virol 75 (Pt 9): 2311-2318.
Kaashoek, M. J., A. Moerman, et al. (1995). "An inactivated vaccine based on a glycoprotein E-negative strain of bovine herpesvirus 1 induces protective immunity and allows serological differentiation." Vaccine 13(4): 342-346.
Kaashoek, M. J. and J. T. Van Oirschot (1996). "Early immunity induced by a live gE-negative bovine herpesvirus 1 marker vaccine." Vet Microbiol 53(1-2): 191-197.
Van Oirschot, J. T., M. J. Kaashoek, et al. (1997). "An enzyme-linked immunosorbent assay to detect antibodies against glycoprotein gE of bovine herpesvirus 1 allows differentiation between infected and vaccinated cattle." J Virol Methods 67(1): 23-34.
Wellenberg, G. J., E. R. Verstraten, et al. (1998). "Detection of bovine herpesvirus 1 glycoprotein E antibodies in individual milk samples by enzyme-linked immunosorbent assays." J Clin Microbiol 36(2): 409-413.
Tyborowska, J., K. Bienkowska-Szewczyk, et al. (2000). "The extracellular part of glycoprotein E of bovine herpesvirus 1 is sufficient for complex formation with glycoprotein I but not for cell-to-cell spread." Arch Virol 145(2): 333-351.
Rijsewijk, F. A., M. J. Kaashoek, et al. (2000). "Epitopes on glycoprotein E and on the glycoprotein E/glycoprotein I complex of bovine herpesvirus 1 are expressed by all of 222 isolates and 11 vaccine strains." Arch Virol 145(5): 921-936.

* cited by examiner

*Primary Examiner* — Zachariah Lucas
*Assistant Examiner* — Nicole Kinsey White
(74) *Attorney, Agent, or Firm* — Bereskin & Parr LLP; Melanie Szweras

(57) ABSTRACT

The present disclosure describes a single chain variable fragment (scFv) that binds BHV-1 virus comprising a light chain variable region, a linker and a heavy chain variable region. The disclosure also describes nucleic acid molecules encoding the scFv molecules, methods and uses thereof for treating or neutralizing BHV-1 infection and diagnostic methods, agents and kits thereof.

21 Claims, 12 Drawing Sheets

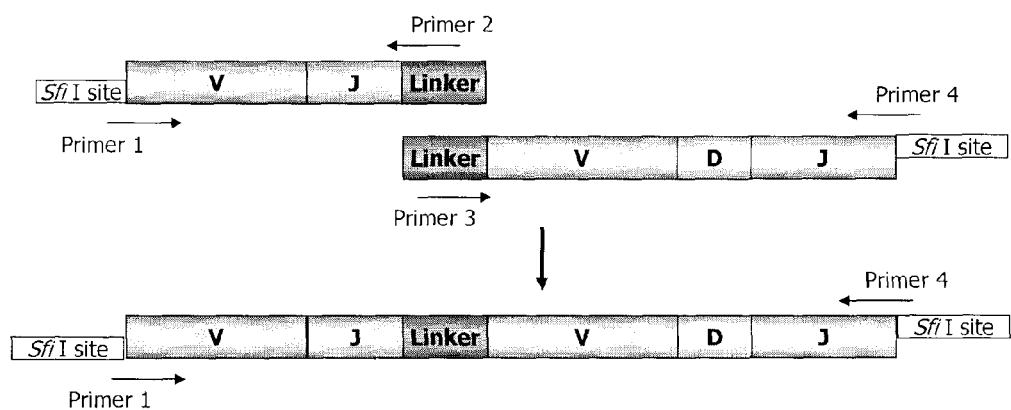
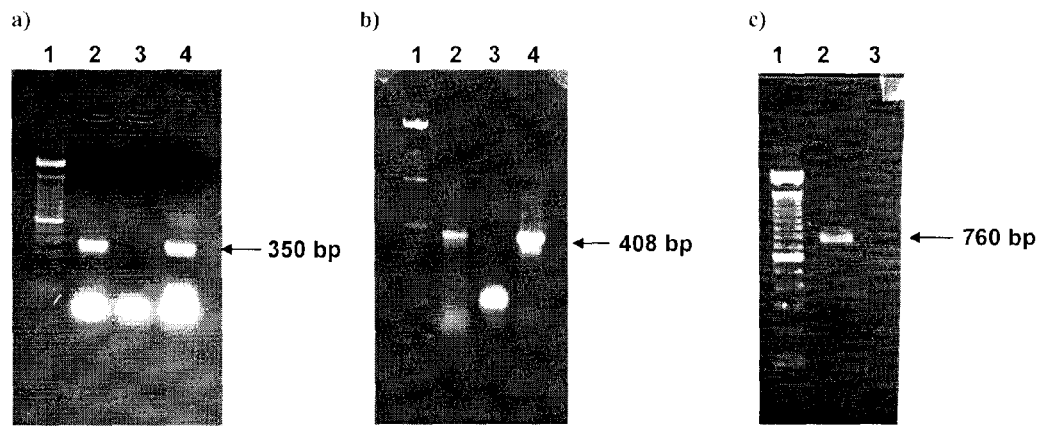
Figure 1

SEQ ID NO:2

QAVLTQPSSVSGSLGQRVSITCSGSSSNIGRYGVGWYQQVPGSGLRRIIYGSVSRPSGVPVRFSGSKSGDTATLTISSLQ 80
AEDEADYFCATADYTSSPVLFGSGTTLTVLGQSSRSSQVQLRESGPSLVKPSQTLSLTCTVSGFSLSGNSVGWVRQTPGK 160
ALEWLGNMDGIGTTDYNPALKSRLSITKDNSKSQVSLSLSSVTTEDTATYYCAKCTGAYCWRFDDAYGYDDWGQGLLVTV 240
SS 242

SEQ ID NO:3

5' CGGCCCAGGCTGTGCTGACTCAGCCGTCCTCCGTGTCCGGCTCCCTGGGCCAGAGGGTCT 60
CCATCACCTGCTCTGGAAGCAGCAGCAACATCGGTAGATATGGTGTGGGCTGGTACCAAC 120
AGGTCCCAGGATCGGGCCTCAGAAGGATCATATATGGTAGTGTCAGTCGACCCTCGGGGG 180
TCCCCGTCCGATTCTCCGGCTCCAAGTCTGGCGACACAGCCACCCTGACCATCAGCTCGC 240
TCCAGGCTGAGGACGAGGCGGATTATTTCTGTGCAACTGCTGACTACACTAGTAGTCCTG 300
TTCTTTTCGGCAGCGGGACCACACTGACCGTCCTAGGTCAGTCCTCTAGATCTTCCCAGG 360
TGCAGCTGCGGGAGTCGGGCCCCAGCCTGGTGAAGCCCTCACAGACCCTGTCCCTCACCT 420
GCACGGTCTCTGGATTCTCATTAAGCGGTAATAGTGTAGGCTGGGTCCGCCAGACTCCAG 480
GAAAGGCGCTGGAGTGGCTCGGTAACATGGATGGTATAGGAACCACAGACTATAACCCAG 540
CCCTGAAATCCCGGCTCAGCATCACCAAGGACAACTCCAAAAGCCAAGTCTCTCTATCAC 600
TGAGCAGCGTAACAACTGAGGACACGGCCACATACTATTGTGCGAAGTGTACTGGTGCTT 660
ATTGCTGGAGGTTTGATGACGCTTATGGTTATGATGACTGGGGCCAAGGACTCCTGGTCA 720
CCGTCTCCTCCACTAGTGGCCAAGC 745 3'

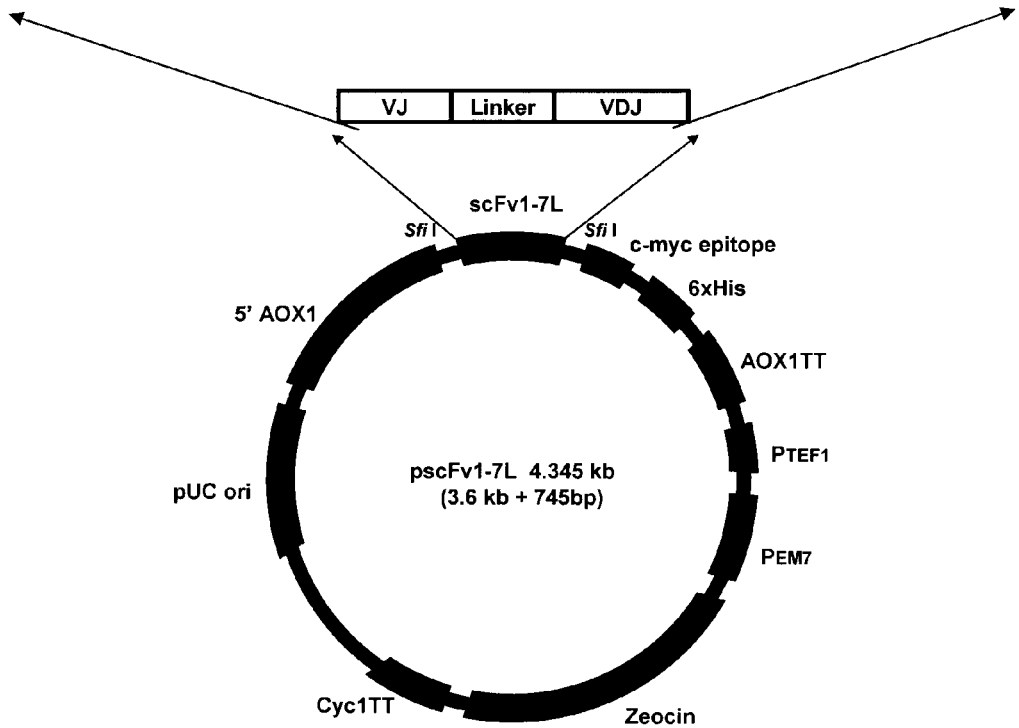

Figure 2 a)
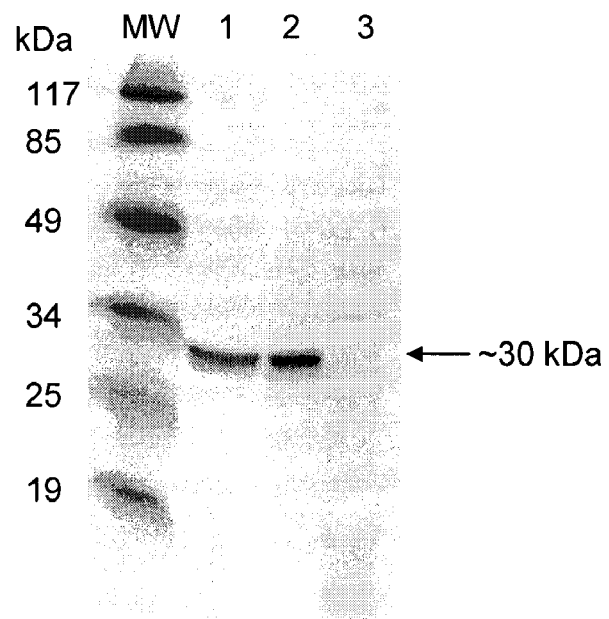
b)
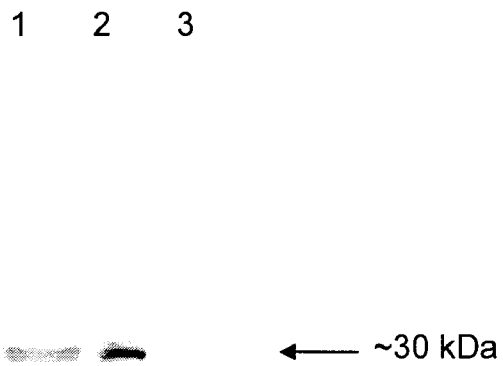
Figure 3 a)
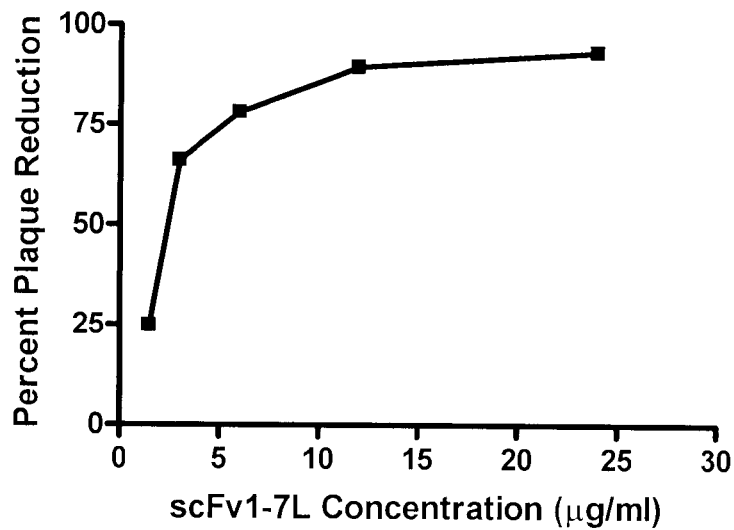
b)
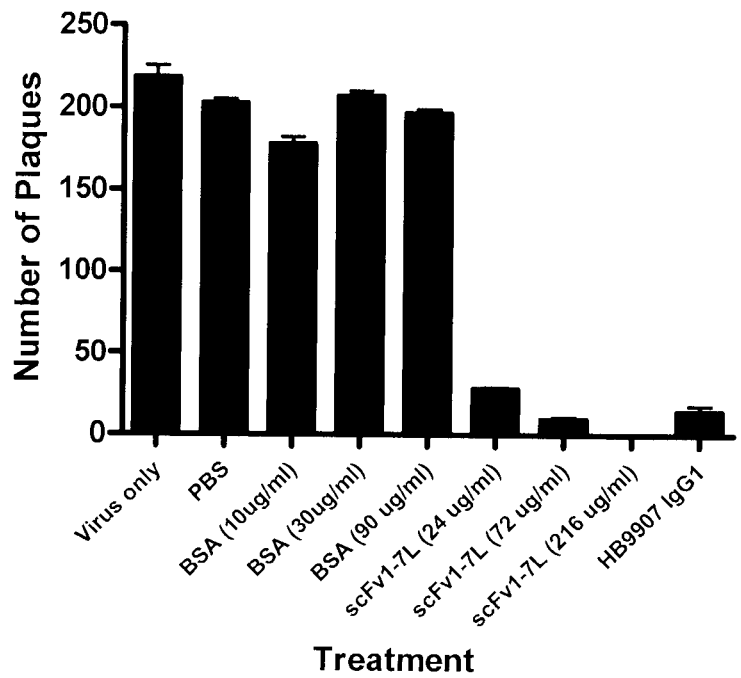
Figure 4 a)
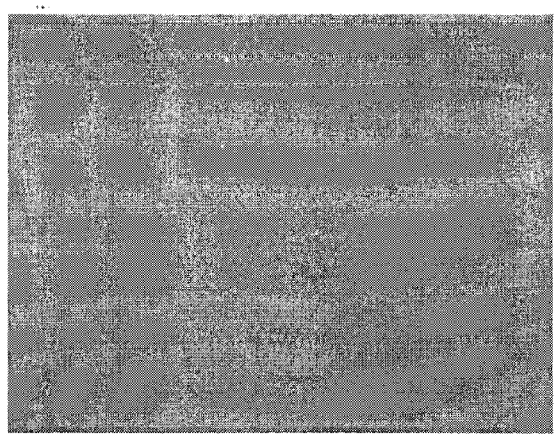
b)
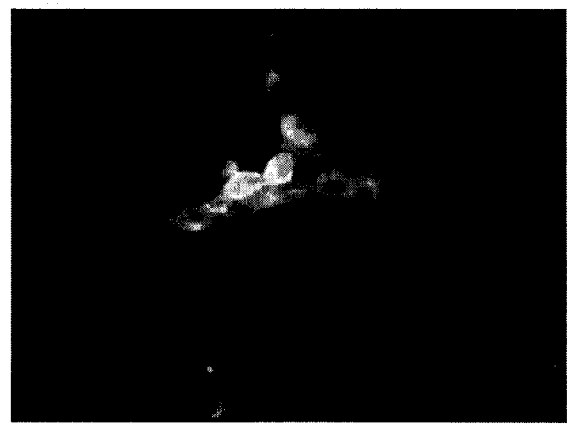
c)
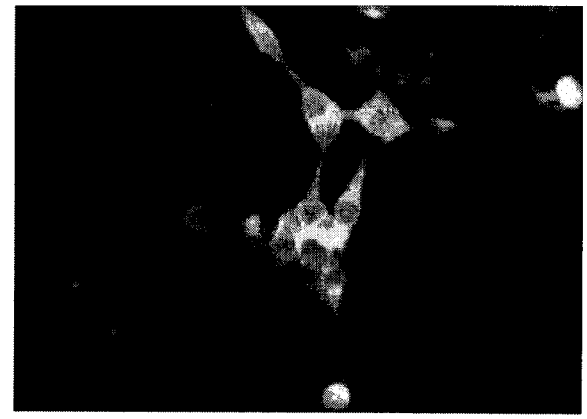
Figure 5

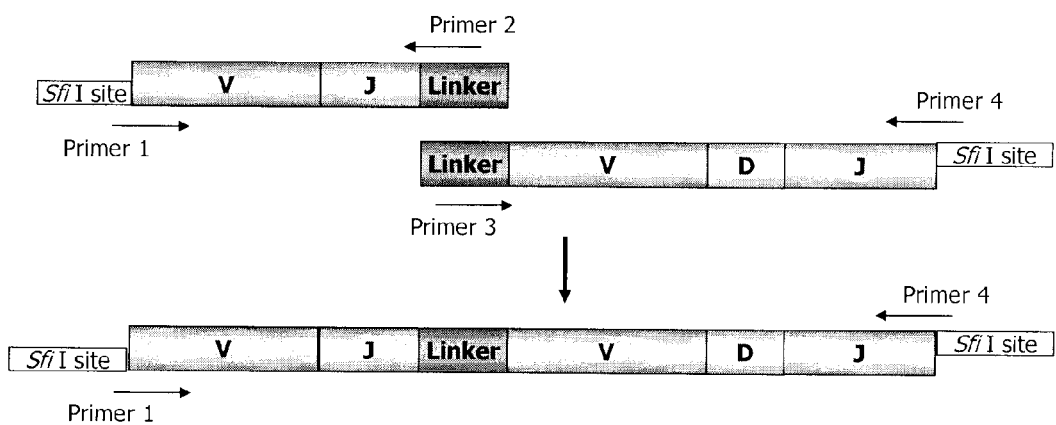
i)
ii)
a)            b)            c)
 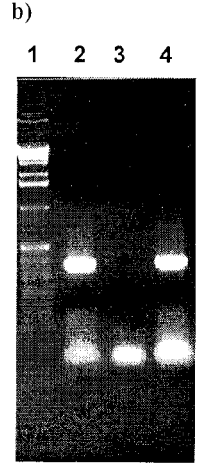 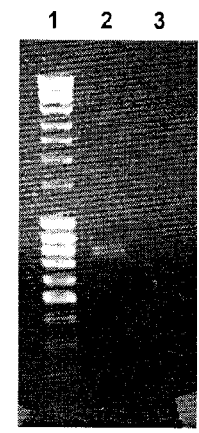
Figure 6

SEQ ID NO:5

QAVLTQPSSVSGSLGQRVSITCSGSSSNIGRYGVGWYQQVPGSGLRRIIYGSVSRPSGVP 60
VRFSGSKSGDTATLTISSLQAEDEADYFCATADYTSSPVLFGSGTTLTVLGQSSRSSSGG 120
GSSGGGGSQVQLRESGPSLVKPSQTLSLTCTVSGFSLSGNSVGWVRQTPGKALEWLGNMD 180
GIGTTDYNPALKSRLSITKDNSKSQVSLSLSSVTTEDTATYYCAKCTGAYCWRFDDAYGY 240
DDWGQGLLVTVSS 253

SEQ ID NO:7

5' CGGCCCAGGCTGTGCTGACTCAGCCGTCCTCCGTGTCCGGCTCCCTGGGCCAGAGGGTCT 60
CCATCACCTGCTCTGGAAGCAGCAGCAACATCGGTAGATATGGTGTGGGCTGGTACCAAC 120
AGGTCCCAGGATCGGGCCTCAGAAGGATCATATATGGTAGTGTCAGTCGACCCTCGGGGG 180
TCCCCGTCCGATTCTCCGGCTCCAAGTCTGGCGACACAGCCACCCTGACCATCAGCTCGC 240
TCCAGGCTGAGGACGAGGCGGATTATTTCTGTGCAACTGCTGACTACACTAGTAGTCCTG 300
TTCTTTTCGGCAGCGGGACCACACTGACCGTCCTAGGTCAGTCCTCTAGATCTTCCAGCG 360
GTGGTGGCAGCTCCGGTGGTGGCGGTTCCCAGGTGCAGCTGCGGGAGTCGGGCCCCAGCC 420
TGGTGAAGCCCTCACAGACCCTGTCCCTCACCTGCACGGTCTCTGGATTCTCATTAAGCG 480
GTAATAGTGTAGGCTGGGTCCGCCAGACTCCAGGAAAGGCGCTGGAGTGGCTCGGTAACA 540
TGGATGGTATAGGAACCACAGACTATAACCCAGCCCTGAAATCCCGGCTCAGCATCACCA 600
AGGACAACTCCAAAAGCCAAGTCTCTCTATCACTGAGCAGCGTAACAACTGAGGACACGG 660
CCACATACTATTGTGCGAAGTGTACTGGTGCTTATTGCTGGAGGTTTGATGACGCTTATG 720
GTTATGATGACTGGGGCCAAGGACTCCTGGTCACCGTCTCCTCCACTAGTGGCCAAGC 778 3'

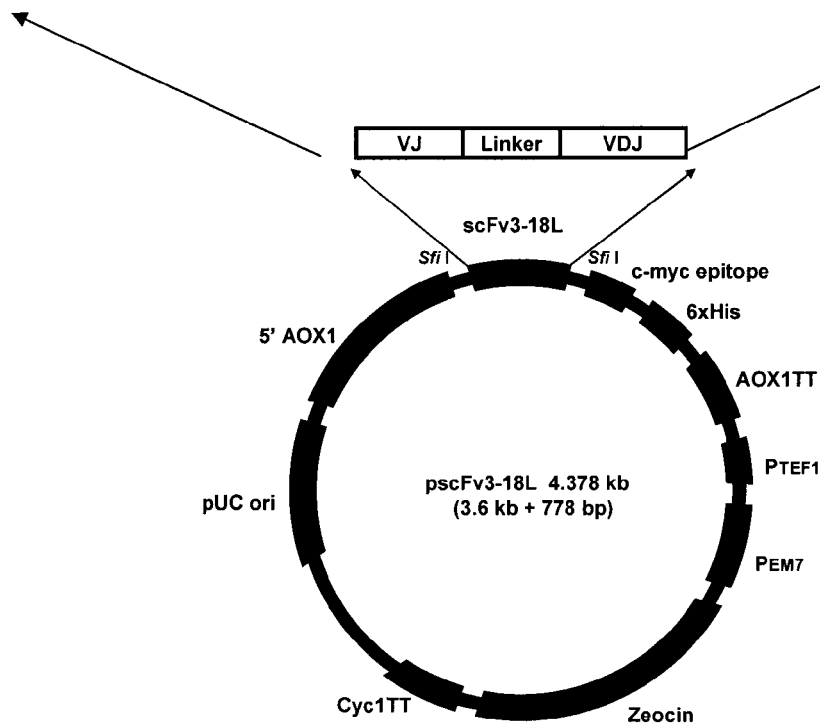

Figure 7

SEQ ID NO:6

QAVLTQPSSVSGSLGQRVSITCSGSSSNIGRYGVGWYQQVPGSGLRRIIYGSVSRPSGVP 60
VRFSGSKSGDTATLTISSLQAEDEADYFCATADYTSSPVLFGSGTTLTVLGQSSRSSGGG 120
GSSGGGGSQVQLRESGPSLVKPSQTLSLTCTVSGFSLSGNSVGWVRQTPGKALEWLGNMD 180
GIGTTDYNPALKSRLSITKDNSKSQVSLSLSSVTTEGTATYYCAKCTGAYCWRFDDAYGY 240
DDWGQGLLVTVSS 253

SEQ ID NO:8

5' CGGCCCAGGCTGTGCTGACTCAGCCGTCCTCCGTGTCCGGCTCCCTGGGCCAGAGGGTCT 60
CCATCACCTGCTCTGGAAGCAGCAGCAACATCGGTAGATATGGTGTGGGCTGGTACCAAC 120
AGGTCCCAGGATCGGGCCTCAGAAGGATCATATATGGTAGTGTCAGTCGACCCTCGGGGG 180
TCCCCGTCCGATTCTCCGGCTCCAAGTCTGGCGACACAGCCACCCTGACCATCAGCTCGC 240
TCCAGGCTGAGGACGAGGCGGATTATTTCTGTGCAACTGCTGACTACACTAGTAGTCCTG 300
TTCTTTTCGGCAGCGGGACCACACTGACCGTCCTAGGTCAGTCCTCTAGATCTTCCGGCG 360
GTGGTGGCAGCTCCGGTGGTGGCGGTTCCCAGGTGCAGCTGCGGGAGTCGGGCCCCAGCC 420
TGGTGAAGCCCTCACAGACCCTGTCCCTCACCTGCACGGTCTCTGGATTCTCATTAAGCG 480
GTAATAGTGTAGGCTGGGTCCGCCAGACTCCAGGAAAGGCGCTGGAGTGGCTCGGTAACA 540
TGGATGGTATAGGAACCACAGACTATAACCCAGCCCTGAAATCCCGGCTCAGCATCACCA 600
AGGACAACTCCAAAAGCCAAGTCTCTCTATCACTGAGCAGCGTAACAACTGAGGGCACGG 660
CCACATACTATTGTGCGAAGTGTACTGGTGCTTATTGCTGGAGGTTTGATGACGCTTATG 720
GTTATGATGACTGGGGCCAAGGACTCCTGGTCACCGTCTCCTCACTAGTGGCCAAGC 778 3'

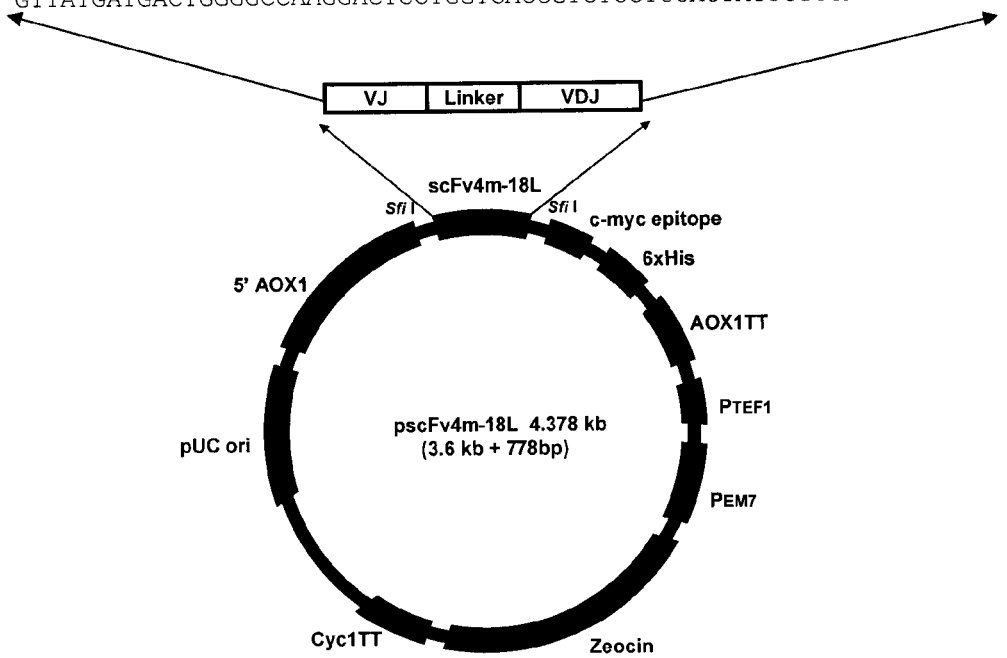

Figure 8 i)
a)
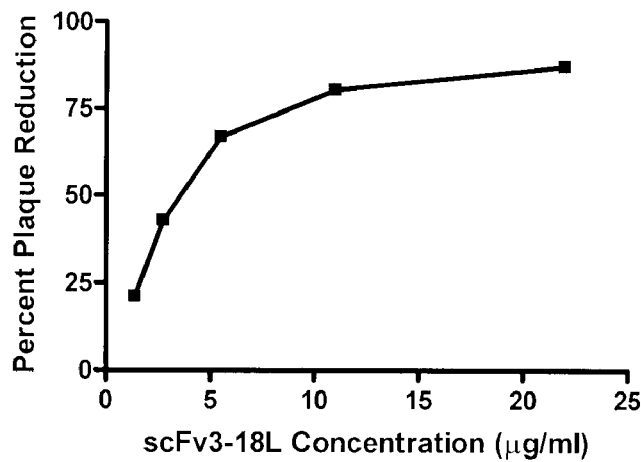
b)
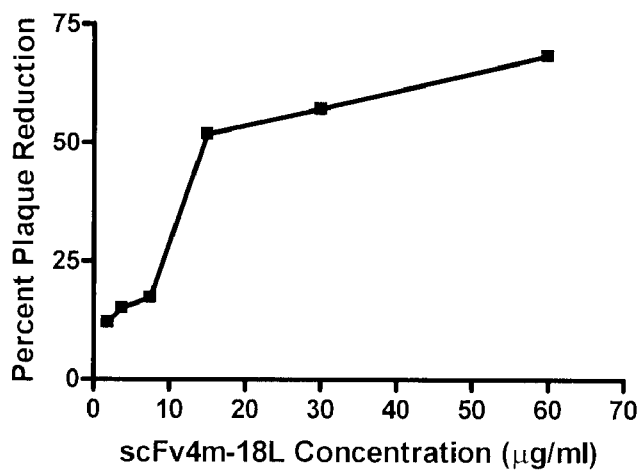
c)
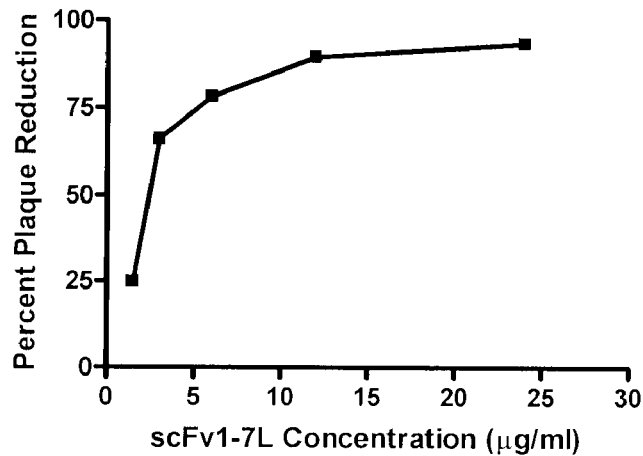
Figure 10

ENGINEERED SCFV AGAINST BOVINE HERPES VIRUS TYPE I

CROSS REFERENCE TO RELATED APPLICATIONS

This is a national stage application of PCT/CA2008/001302 filed on Jul. 18, 2008 which claims priority from U.S. provisional application 60/950,638 filed on Jul. 19, 2007, both of which are incorporated herein by reference in their entirety.

FIELD OF THE DISCLOSURE

The disclosure relates to novel engineered scFv molecules against bovine herpes virus Type-1 (BHV-1). In particular, the disclosure relates to compositions and methods and uses thereof for recognizing and neutralizing BHV-1 virus as well as for immunodiagnostic and therapeutic protection in cattle.

BACKGROUND OF THE DISCLOSURE

The bovine herpes virus Type-1 (BHV-1), an alpha herpes virus, is an important etiological agent of respiratory (infectious bovine rhinotracheitis; IBR), and genital, (infectious pustular vulvovaginits; IPV), diseases in cattle (Gibbs and Rweyemamy, 1977; Schwyzer and Ackermann, 1996). BHV-1 infection costs $100 million to Canadian and up to $500 million to American cattle industry. BHV-1 is also associated with bovine respiratory disease complex (BRDC) resulting from subsequent secondary bacterial infections and costs the U.S. cattle industry up to 3 billion dollars annually (Jones and Chowdhury, 2007). This hampers dairy and beef trade with BHV-1 free countries for instance those within the European Union, where BHV-1 eradication efforts are being made.

The respiratory form of the disease spreads via aerosols and is characterized by rhinotracheitis, conjunctivitis, and development of bovine respiratory disease (BRD) complex complicated by secondary bacterial infections. The predisposition to bacterial complications by the virus is related directly to its cytolytic effect on the cells of nasal and tracheal mucosa apart from its immunosuppressive effects. The genital infection spreads via genital secretions, semen and foetal fluids and is manifested as IPV, balanoposthitis, endometritis and abortions (Yates, 1982; Tikoo et al., 1995; Thiry et al. 2006). During the abortion storm that commonly follows respiratory and conjunctival disease, up to 60% of herd may abort due to this virus. The BHV-1 may also be transmitted via contaminated cryo-preserved semen during artificial insemination (Jones, 1998, 2003). The virus replicates in local mucus membranes and neurons of trigeminal and sacral ganglia where it survives in the host as latent infection but gets activated during stressful conditions such as transportation and parturition.

Such disease outbreaks are due to lack of an effective vaccine result in viral latency and viral shedding. This necessitates the use of antibiotics to prevent secondary bacterial infections that lower the quality of milk and beef.

The currently used inactivated and modified live vaccines (MLVs); (Van Donkersgoed et al, 1991; van Drunen Littel-van den Hurk, 2006) do not confer adequate protection against BHV-1 infection. The MLVs not only result in viral latency but also cause abortions in pregnant animals (Van Donkersgoed and Klassen, 1995). Prior immunization of calves against BHV-1 does not reduce the risk of infection since viral outbreaks have been reported in feed lot calves in Canada (Van Donkersgoed and Klassen, 1995).

Since no effective vaccines are available to prevent latency and viral shedding in a herd, passive immunization with virus neutralizing antibodies could provide an effective adjunct approach for prevention and control of BHV-1 infection in addition to conventional immunization. The monoclonal IgG1 antibody that neutralizes BHV-1 virus has been developed which is capable of providing protective immunity (Levings and Stoll, 1991).

The hetero-tetrameric immunoglobulin molecule provides remarkable intra-molecular synergy in the context of antigen recognition by the antigen binding fragment (Fab) at the amino terminal end as well as biological effector functions via crystallizable fragment (Fc) at the carboxy terminal end. Antibodies provide the most successful class of targeted therapeutics in addition to their application in specific clinical or immunodiagnosis of various diseases. Antibody engineering has its origins in hybridoma technology which converts B lymphocytes from an immunized animal or subject into hybrid cell lines that have acquired the ability to produce monoclonal antibodies (Kohler and Milstein, 1975). Indeed, monoclonal antibodies have become indispensable in immunodiagnostics together with significant therapeutic potential via innovative recombinant DNA technologies such as chimerization and humanization of antibodies (Morrison et al., 1984; Boulianne et al, 1984). The isolation of antibodies from hybridomas, however, has its limitations with regard to stability and expression level. These limitations can be circumvented by developing combinatorial libraries of single chain variable fragment of an antibody (scFv) or as fragment antigen-binding (Fab) that could be successfully expressed in microrganisms (Winter et al., 1994; Harvey et al., 2004). Such a dissection of antibodies into minimal antigen binding fragments has certain advantages as these can be fused with a range of molecules including toxins for the treatment of cancer or other infectious and inflammatory diseases (Morrison et al., 1984; Boulianne et al, 1984; Carter, 2001). A wide variety of redesigned mAbs of minimal antigen binding fragments provide novel reagents for immunotherapy, medical imaging and immunodiagnostics (Maynard and Georgiou, 2000). Essentially, scFv where $V_H$ and $V_L$ domains are connected via flexible polypeptide, have been shown to retain the specific monovalent antigen binding affinity of the parent antibody with improved pharmacokinetics for tissue penetration (Bird et al., 1988; Huston et al., 1988; Brinkmann et al., 1995). However, influences of linker size are difficult to predict without the knowledge of the 3-dimensional structure of the recombinant proteins in question.

SUMMARY OF THE DISCLOSURE

The present inventors have developed novel engineered antibodies as single chain variable fragments (scFv) against BHV-1. These novel scFv molecules have use in prevention and therapy via systemic and mucosal application or immunization (for example, by nasal or vaginal application) during transportation and in animal management.

Accordingly, the present disclosure provides a single chain variable fragment (scFv) that binds BHV-1 virus comprising (a) a light chain variable region; (b) a linker; and (c) a heavy chain variable region. In one embodiment, the linker is a polypeptide linker. In another embodiment, the linker comprises one or more glycine and/or serine amino acid residues. In an embodiment, the linker comprises 2-20 amino acids. In one embodiment, the linker comprises 4-8 amino acids, preferably 7 amino acids. In a particular embodiment, the linker comprises the amino acid sequence GQSSRSS (SEQ ID NO:1). In another particular embodiment, the scFv comprises the amino acid sequence as shown in SEQ ID NO:2, or a variant thereof; or is encoded by the nucleotide sequence as shown in SEQ ID NO:3, or a variant thereof.

In another embodiment, the linker comprises 15-20 amino acids, preferably 18 amino acids. In a particular embodiment, the linker comprises the amino acid sequence GQSSRSSSGGGSSGGGGS (SEQ ID NO:4). In another particular embodiment, the scFv comprises the amino acid sequence as shown in SEQ ID NO:5 or 6, or a variant thereof; or is encoded by the nucleotide sequence as shown in SEQ ID NO:7 or 8, or a variant thereof.

In another aspect, there is provided an isolated nucleic acid encoding the scFv disclosed herein. In one embodiment, the isolated nucleic acid encodes a single chain variant against BHV-1 comprising the amino acid sequence as shown in SEQ ID NO:2, SEQ ID NO:5 and/or SEQ ID NO:6 or variants thereof. In another embodiment, the isolated nucleic acid comprises the nucleotide sequence as shown in SEQ ID NO:3, SEQ ID NO:7 and/or SEQ ID NO:8 or variants thereof.

In a further aspect, there is provided a recombinant expression vector comprising the isolated nucleic acid molecule. In yet a further aspect, there is provided a host cell comprising the nucleic acid molecule or the recombinant expression vector.

In yet another aspect, there is provided a composition comprising the scFv disclosed herein and a pharmaceutically acceptable excipient, carrier, buffer or stabilizer.

In a further aspect, there is provided a use of an effective amount of the scFv disclosed herein for the treatment of BHV-1 infection in cattle. In one embodiment, there is provided a method of treating BHV-1 infection in cattle, comprising administering an effective amount of the scFv disclosed herein to a cow in need thereof. In another embodiment, there is provided a use of the scFv disclosed herein in the preparation of a medicament for treating BHV-1 infection in cattle. In yet another embodiment, there is provided a scFv disclosed herein for use in treating BHV1 infection in cattle.

In yet a further aspect, there is provided a use of an effective amount of the scFv disclosed herein for neutralizing BHV-1 in cattle, preferably in infected semen of the cattle. In one embodiment, there is provided a method of neutralizing BHV-1 in cattle, comprising administering an effective amount of the scFv disclosed herein to a cow in need thereof. In another embodiment, there is provided a use of the scFv disclosed herein in the preparation of a medicament for neutralizing BHV-1 in cattle. In yet another embodiment, there is provided a scFv disclosed herein for use in neutralizing BHV1 in cattle.

In a further embodiment, the methods and uses are for treating bovine respiratory disease (IBR) or bovine genital disease (IPV). In another embodiment, the methods and uses are for treating BHV-1 during transportation or parturition. In one embodiment, the treatment is via passive immunization. The scFv may be used or administered intranasally, intravaginally, by injection or mucosally. In another embodiment, scFv is used or administered in conjunction with conventional immunization, such as inactivated or modified live vaccines.

In another aspect, there is provided a kit for treating or diagnosing bovine respiratory disease comprising an effective amount of the scFv described herein and directions for use thereof.

In yet another aspect, there is provided a method of detecting BHV-1 infection in a cow comprising assaying a sample from the cow for binding with an scFv described herein, wherein binding by the scFv is indicative of the cow being infected with BHV-1. In a further aspect, there is provided a method of determining whether a cow is vaccinated comprising assaying a sample from the cow for binding with an scFv described herein, wherein binding by the scFv is indicative of a vaccinated cow and lack of binding is indicative of an unvaccinated cow. In one embodiment, the sample is assayed by an immunoassay.

In another aspect, there is provided a diagnostic agent comprising (1) a scFv that binds to a BHV-1 described herein attached to (2) a label that produces a detectable signal, directly or indirectly. In one embodiment, the label is a radioisotope, a fluorescent compound, a chemiluminescent compound, an enzyme, an imaging agent or a metal ion. In another embodiment, there is provided a kit comprising the diagnostic agent and instructions for use thereof.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

The disclosure will now be described in relation to the drawings in which:

FIG. 1 shows i) the strategy for VJ-linker-VDJ overlap PCR amplification and ii) the PCR amplification of VJ (a) and VDJ (b) and overlap PCR (c) from cDNA isolated from HB-9907 hybridoma secreting anti-BHV-1 IgG1. a) Lane 1, 100-bp DNA ladder; Lane 2, positive VJ control (BLV10H8 hybridoma); Lane 3, Negative control; Lane 4, HB-9907 hybridoma VJ PCR product. b) Lane 1, 1-kb DNA ladder; Lane 2, positive VDJ control (BLV10H8 hybridoma); Lane 3, negative control; Lane 4, HB-9907 hybridoma VDJ PCR product. c) Lane 1, 100-bp DNA ladder; Lane 2, Overlap (VJ-7 amino acid linker-VDJ) PCR product; Lane 3, negative control.

FIG. 2 shows the nucleotide sequence of VJ-7 amino acid linker-VDJ overlap PCR product upon cloning into pPICZα expression vector (SEQ ID NO:3) and the amino acid sequence (SEQ ID NO:2). Linker sequence is underlined.

FIG. 3 shows a) a Coomassie blue stained 12% SDS-PAGE gel. Lane 1, unpurified scFv1-7L; Lane 2, purified scFv1-7L; Lane 3, negative control, X-33 P. pastoris supernatant. b) Western immunoblot demonstrating detection of recombinant scFv1-7L; unpurified scFv1-7L (Lane 1); purified scFv1-7L (Lane 2); and negative control, X-33 P. pastoris supernatant (Lane 3).

FIG. 4 shows virus neutralization (end point 50%) of BHV-1 virus by recombinant scFv1-7L protein. a) Percent plaque inhibition is calculated on the basis of non-specific inhibition by heterologous protein BSA and b) mean plaque reduction as a result of scFv1-7L treatment in two independent experiments.

FIG. 5 shows immunodetection of BHV-1 viral antigens in MDBK cells infected with BHV-1 (Wyoming strain). Note cytoplasmic fluorescence in BHV-I infected MDBK cells stained with HB-9907 anti-BHV-1 IgG1 antibody (b) and recombinant scFv1-7L (c) as compared to negative control (a). Magnification 400×

FIG. 6 shows i) the strategy for VJ-linker-VDJ PCR amplification and ii) the PCR amplification of VDJ (a) and VJ (b)

Figure 9:
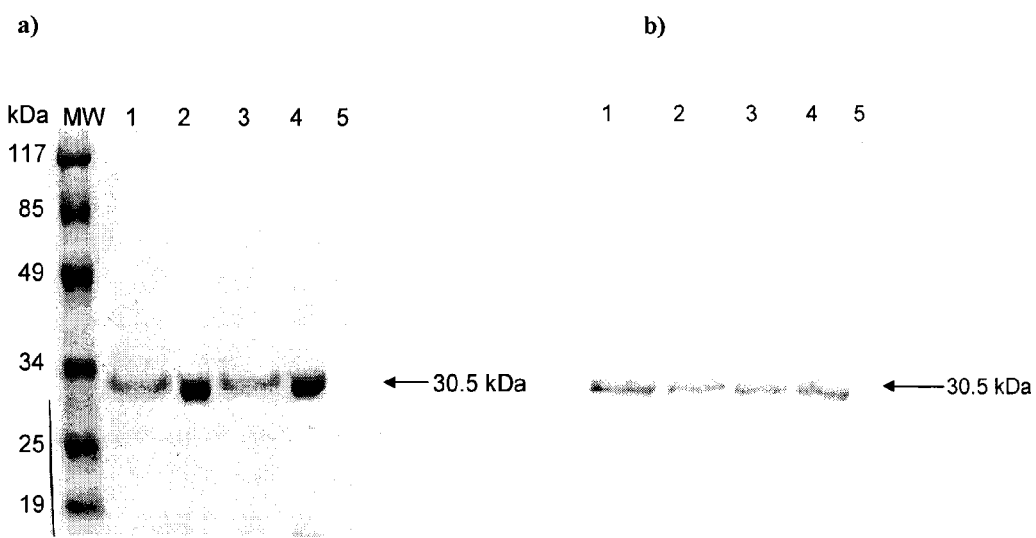

and overlap PCR (c) from cDNA isolated from HB-9907 hybridoma secreting anti-BHV-1 IgG1. a) Lane 1, 1-kb DNA ladder; Lane 2, positive VDJ control (BLV10H8 hybridoma); Lane 3, Negative control; Lane 4, HB-9907 hybridoma VDJ PCR product. b) Lane 1, 1-kb DNA ladder; Lane 2, positive VJ control (BLV10H8 hybridoma); Lane 3, negative control; Lane 4, HB-9907 hybridoma VJ PCR product. c) Lane 1, 1-kb DNA ladder; Lane 2, Overlap (VJ-18 amino acid linker-VDJ) PCR product; Lane 3, negative control.

FIG. 7 shows the nucleotide sequence of VJ-18 amino acid linker-VDJ, overlap PCR product upon cloning into pPICZα expression vector (SEQ ID NO:7) and the amino acid sequence (SEQ ID NO:5). The linker sequence is underlined.

FIG. 8 shows the nucleotide sequence of VJ-18 amino acid linker-VDJ (mutation in FR3), overlap PCR product upon cloning into pPICZα expression vector (SEQ ID NO:8) and the amino acid sequence (SEQ ID NO:6). The linker sequence is underlined. The mutation in FR3 is bolded and underlined.

FIG. 9 shows a) the recombinant scFv3-18L and scFv4m-18L analyzed on 12% SDS-PAGE stained with Coomassie blue: Lane 1 unpurified scFv3-18L; Lane 2 purified scFv3-18L; Lane 3, unpurified scFv4m-18L; Lane 4, purified scFv4m-18L; Lane 5, KM71H *P. pastoris* supernatant negative for recombinant proteins; and b) a Western immunoblot for detection of recombinant scFv3-18L and scFv4m-18L proteins. Lane 1, unpurified scFv3-18L; Lane 2, purified scFv3-18L; Lane 3, unpurified scFv4m-18L; Lane 4, purified scFv4m-18L; Lane 5, KM71H *P. pastoris* supernatant negative for recombinant proteins.

FIG. 10 shows i) virus neutralization (end point 50%) of BHV-1 virus by recombinant scFv3-18L (a) scFv4m-18L (b) and scFv1-7L (c) proteins; and ii) mean plaque reduction as a result of treatment with scFv3-18L, scFv4m-18L, and scFv1-7L in two independent experiments.

FIG. 11 shows immunodetection of BHV-1 viral antigens in a mixture of BHV-1 infected and uninfected MDBK cells in each field. Note cytoplasmic fluorescence in BHV-1 infected MDBK cells stained with HB-9907 anti-BHV-1 IgG1 antibody (b), negative control (a), scFv3-18L (c), scFv4m-18L (d) and scFv-17L (e). Magnification 400×.

DETAILED DESCRIPTION OF THE DISCLOSURE

The present inventors constructed scFvs from bovine IgG1 neutralizing antibody against BHV-1 with either a 7- or 18-amino acid linker and have shown that both scFvs are capable of viral neutralization and antigen recognition similar to the parent monoclonal IgG1 antibody against BHV-1 virus.

Proteins and Nucleic Acids:

Accordingly, the present disclosure provides a single chain variable fragment (scFv) that binds BHV-1 virus comprising (a) a light chain variable region; (b) a linker; and (c) a heavy chain variable region. The order of the light chain variable region ($V_L$) and the heavy chain variable region ($V_H$) relative to the linker (L) can be either $V_L$-L-$V_H$ or $V_H$-L-$V_L$, preferably $V_L$-L-$V_H$.

The term "BHV-1 virus" refers to bovine herpes virus Type I which is an alpha herpes virus that causes respiratory and genital disease in cattle.

The term "scFv" as used herein means a single chain variable fragment that comprises a light chain variable region and a heavy chain variable region joined by a linker. The term "scFv that binds BHV-1 virus" means a single chain variable fragment that has specificity for BHV-1. The $V_L$ and $V_H$ regions may be derived from a BHV-1 antibody or may be chemically or recombinantly synthesized. The scFv may include dsFv, ds-scFv, dimers, diabodies or multimers of scFvs described herein.

To produce monoclonal antibodies from which the variable regions may be derived, antibody producing cells (lymphocytes) can be harvested from a cow infected with BHV-1 and fused with myeloma cells by standard somatic cell fusion procedures (Saini et al., 1997) thus immortalizing these cells and yielding hybridoma cells. Such techniques are well known in the art, (e.g. the hybridoma technique originally developed by Kohler and Milstein (*Nature* 256:495-497 (1975)) as well as other techniques such as the human B-cell hybridoma technique (Kozbor et al., *Immunol. Today* 4:72 (1983)), the EBV-hybridoma technique to produce human monoclonal antibodies (Cole et al., *Methods Enzymol,* 121: 140-67 (1986)), and screening of combinatorial antibody libraries (Huse et al., *Science* 246:1275 (1989)). Hybridoma cells can be screened immunochemically for production of antibodies specifically reactive with BHV-1 and the monoclonal antibodies can be isolated.

Specific antibodies, or antibody fragments, reactive against BHV-1, may also be generated by screening expression libraries encoding immunoglobulin genes, or portions thereof, expressed in bacteria with cell surface components. For example, complete Fab fragments, VH regions and FV regions can be expressed in bacteria using phage expression libraries (See for example Ward et al., *Nature* 341:544-546 (1989); Huse et al., *Science* 246:1275-1281 (1989); and McCafferty et al., *Nature* 348:552-554 (1990)).

The term "linker" as used herein includes, without limitation, peptide linkers. The peptide linker can be any size provided it does not interfere with the binding of the BHV-1 virus by the variable regions. In one embodiment, the linker comprises one or more glycine and/or serine amino acid residues. The linker may be any size that does not interfere with the binding of the $V_H$ and $V_L$ regions to BHV-1. The linker is preferably 2-20 amino acids.

In an embodiment, the linker comprises 4-8 amino acids, preferably 7 amino acids. In a particular embodiment, the linker comprises the amino acid sequence GQSSRSS (SEQ ID NO:1). In another embodiment, the linker comprises 15-20 amino acids, preferably 18 amino acids. In a particular embodiment, the linker comprises the amino acid sequence GQSSRSSSGGGSSGGGGS (SEQ ID NO:4).

In one embodiment, the scFv comprises the amino acid sequence as shown in SEQ ID NO:2, or a variant thereof; or is encoded by the nucleotide sequence as shown in SEQ ID NO:3, or a variant thereof. In another embodiment, the scFv comprises the amino acid sequence as shown in SEQ ID NO:5 or 6 or a variant thereof; or is encoded by the nucleic acid sequence as shown in SEQ ID NO: 7 or 8 or a variant thereof.

In another aspect, there is provided an isolated nucleic acid encoding the scFv disclosed herein. In one embodiment, the isolated nucleic acid encodes a single chain variant against BHV-1 comprising the amino acid sequence as shown in SEQ ID NO:2, SEQ ID NO:5 and/or SEQ ID NO:6 or a variant thereof. In another embodiment, the isolated nucleic acid comprises the nucleotide sequence as shown in SEQ ID NO:3, SEQ ID NO:7 and/or SEQ ID NO:8 or a variant thereof.

The term "nucleic acid sequence" as used herein refers to a sequence of nucleoside or nucleotide monomers consisting of naturally occurring bases, sugars and intersugar (backbone) linkages. The term also includes modified or substituted sequences comprising non-naturally occurring monomers or portions thereof. The nucleic acid sequences of the present application may be deoxyribonucleic acid sequences (DNA)

or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine.

The term "isolated nucleic acid sequences" as used herein refers to a nucleic acid substantially free of cellular material or culture medium when produced by recombinant DNA techniques, or chemical precursors, or other chemicals when chemically synthesized. An isolated nucleic acid is also substantially free of sequences which naturally flank the nucleic acid (i.e. sequences located at the 5' and 3' ends of the nucleic acid) from which the nucleic acid is derived. The term "nucleic acid" is intended to include DNA and RNA and can be either double stranded or single stranded, and represents the sense or antisense strand. Further, the term "nucleic acid" includes the complementary nucleic acid sequences.

The term "complementary" refers to nucleic acid sequences capable of base-pairing according to the standard Watson-Crick complementary rules, or being capable of hybridizing to a particular nucleic acid segment under stringent conditions.

The term "amino acid" includes all of the naturally occurring amino acids as well as modified amino acids.

The term "isolated polypeptides" refers to a polypeptide substantially free of cellular material or culture medium when produced by recombinant DNA techniques, or chemical precursors or other chemicals when chemically synthesized.

The term "variant" as used herein includes modifications, derivatives, or chemical equivalents of the amino acid and nucleic acid sequences disclosed herein that perform substantially the same function as the polypeptides or nucleic acid molecules disclosed herein in substantially the same way. For instance, the variants have the same function of being able to bind to BHV-1; and/or neutralize BHV-1. In one embodiment, variants of polypeptides disclosed herein include, without limitation, conservative amino acid substitutions. Variants of polypeptides also include additions and deletions to the polypeptide sequences disclosed herein. In addition, variant nucleotide sequences and polypeptide sequences include analogs and derivatives thereof. In another embodiment, the variants include polypeptides that can bind to the same epitope or antigen recognized by the isolated light chain variable regions and isolated heavy chain variable regions disclosed herein.

A "conservative amino acid substitution" as used herein, is one in which one amino acid residue is replaced with another amino acid residue without abolishing the protein's desired properties.

The term "derivative of a peptide" refers to a peptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine.

In one embodiment, the variant amino acid sequences have at least 50%, preferably at least 60%, more preferably at least 70%, most preferably at least 80%, even more preferably at least 90%, and even most preferably 95% sequence identity to SEQ ID NOs:2, 5 or 6. In another embodiment, variant nucleic acid sequences include nucleic acid sequences that hybridize to SEQ ID NOs:3, 7 or 8 or the nucleic acid sequences encoding the amino acid sequences of SEQ ID NOS:2, 5 or 6 under at least moderately stringent hybridization conditions, or have at least 50%, 60%, 70%, 80%, 90% or 95% sequence identity to SEQ ID NOs:3, 7 or 8 or the nucleic acid sequences that encode the amino acid sequence of SEQ ID NOS:2, 5 or 6.

The term "sequence identity" as used herein refers to the percentage of sequence identity between two polypeptide sequences or two nucleic acid sequences. To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions.times.100%). In one embodiment, the two sequences are the same length. The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules of the present application. BLAST protein searches can be performed with the XBLAST program parameters set, e.g., to score-50, wordlength=3 to obtain amino acid sequences homologous to a protein molecule of the present invention. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). Another preferred, non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.−16.6 (Log 10 [Na+])+0.41(% (G+C)−600/l), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm−5° C. based on the above equation, followed by a wash of 0.2×SSC/0.1% SDS at 60° C. Moderately stringent hybridization conditions include a washing step in 3×SSC at 42° C. It is understood, however, that equivalent stringencies may be achieved using alternative buffers, salts and temperatures. Additional guidance regarding hybridization conditions may be found in: Current Protocols in Molecular Biology, John Wiley & Sons, N.Y., 2002, and in: Sambrook et al., Molecular Cloning: a Laboratory Manual, Cold Spring Harbor Laboratory Press, 2001.

A person skilled in the art will appreciate that the scFvs disclosed herein, as well as the light and heavy chain variable regions, disclosed herein, may be prepared in any of several ways, including without limitation, recombinant and chemical methods.

The nucleic acid molecules disclosed herein may be incorporated in a known manner into an appropriate expression vector which ensures good expression of the scFv polypeptides. Possible expression vectors include but are not limited to cosmids, plasmids, or modified viruses (e.g. replication defective retroviruses, adenoviruses and adeno-associated viruses), so long as the vector is compatible with the host cell used. The expression vectors are "suitable for transformation of a host cell", which means that the expression vectors contain a nucleic acid molecule and regulatory sequences selected on the basis of the host cells to be used for expression, which is operatively linked to the nucleic acid molecule. Operatively linked is intended to mean that the nucleic acid is linked to regulatory sequences in a manner which allows expression of the nucleic acid.

The application therefore includes a recombinant expression vector containing a nucleic acid molecule disclosed herein, or a fragment thereof, and the necessary regulatory sequences for the transcription and translation of the inserted protein-sequence.

Suitable regulatory sequences may be derived from a variety of sources, including bacterial, fungal, viral, mammalian, or insect genes (For example, see the regulatory sequences described in Goeddel, Gene Expression Technology Methods in Enzymology 185, Academic Press, San Diego, Calif. (1990)). Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

The recombinant expression vectors may also contain a selectable marker gene which facilitates the selection of host cells transformed or transfected with a recombinant molecule disclosed herein. Examples of selectable marker genes are genes encoding a protein such as G418 and hygromycin which confer resistance to certain drugs, β-galactosidase, chloramphenicol acetyltransferase, firefly luciferase, or an immunoglobulin or portion thereof such as the Fc portion of an immunoglobulin preferably IgG. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of the recombinant expression vectors disclosed herein and in particular to determine the effect of a mutation on expression and phenotype. It will be appreciated that selectable markers can be introduced on a separate vector from the nucleic acid of interest.

The recombinant expression vectors may also contain genes which encode a fusion moiety which provides increased expression of the recombinant protein; increased solubility of the recombinant protein; and aid in the purification of the target recombinant protein by acting as a ligand in affinity purification, for example, histidine tags and c-myc epitopes. Typical fusion expression vectors include pGEX (Amrad Corp., Melbourne, Australia), pMal (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

Recombinant expression vectors can be introduced into host cells to produce a transformed host cell. The terms "transformed with", "transfected with", "transformation" and "transfection" are intended to encompass introduction of nucleic acid (e.g. a vector) into a cell by one of many possible techniques known in the art. The term "transformed host cell" as used herein is intended to also include cells capable of glycosylation that have been transformed with a recombinant expression vector disclosed herein. Prokaryotic cells can be transformed with nucleic acid by, for example, electroporation or calcium-chloride mediated transformation. For example, nucleic acid can be introduced into mammalian cells via conventional techniques such as calcium phosphate or calcium chloride co-precipitation, DEAE-dextran mediated transfection, lipofectin, electroporation or microinjection. Suitable methods for transforming and transfecting host cells can be found in Sambrook et al. (Molecular Cloning: A Laboratory Manual, 3rd Edition, Cold Spring Harbor Laboratory Press, 2001), and other laboratory textbooks.

Suitable host cells include a wide variety of eukaryotic host cells and prokaryotic cells. For example, polypeptides disclosed herein may be expressed in yeast cells or mammalian cells. Other suitable host cells can be found in Goeddel, Gene Expression Technology: Methods in Enzymology 185, Academic Press, San Diego, Calif. (1990). In addition, the polypeptides disclosed herein may be expressed in prokaryotic cells, such as *Escherichia coli* (Zhang et al., Science 303(5656): 371-3 (2004)). In addition, a *Pseudomonas* based expression system such as *Pseudomonas fluorescens* can be used (US Patent Application Publication No. US 2005/0186666, Schneider, Jane C et al.).

Yeast and fungi host cells suitable for carrying out the methods disclosed herein include, but are not limited to *Saccharomyces cerevisiae*, the genera *Pichia* or *Kluyveromyces* and various species of the genus *Aspergillus*. Examples of vectors for expression in yeast *S. cerevisiae* include pYepSec1 (Baldari. et al., Embo J. 6:229-234 (1987)), pMFa (Kurjan and Herskowitz, Cell 30:933-943 (1982)), pJRY88 (Schultz et al., Gene 54:113-123 (1987)), and pYES2 (Invitrogen Corporation, San Diego, Calif.). Protocols for the transformation of yeast and fungi are well known to those of ordinary skill in the art (see Hinnen et al., Proc. Natl. Acad. Sci. USA 75:1929 (1978); Ito et al., J. Bacteriology 153:163 (1983), and Cullen et al. (Nat Bio/Tech 5:369 (1987)). In one embodiment, the host cell is a *Pichia pastoris* cell.

Suitable mammalian cells include, among others: COS (e.g., ATCC No. CRL 1650 or 1651), BHK (e.g. ATCC No. CRL 6281), CHO (ATCC No. CCL 61), HeLa (e.g., ATCC No. CCL 2), 293 (ATCC No. 1573) and NS-1 cells. Suitable expression vectors for directing expression in mammalian cells generally include a promoter (e.g., derived from viral material such as polyoma, Adenovirus 2, cytomegalovirus and Simian Virus 40), as well as other transcriptional and translational control sequences. Examples of mammalian expression vectors include pCDM8 (Seed, B., Nature 329: 840 (1987)) and pMT2PC (Kaufman et al., EMBO J. 6:187-195 (1987)).

Given the teachings provided herein, promoters, terminators, and methods for introducing expression vectors of an appropriate type into plant, avian, and insect cells may also be readily accomplished. For example, within one embodiment, the polypeptides disclosed herein may be expressed from plant cells (see Sinkar et al., J. Biosci (Bangalore) 11:47-58 (1987), which reviews the use of *Agrobacterium rhizogenes* vectors; see also Zambryski et al., Genetic Engineering, Principles and Methods, Hollaender and Setlow (eds.), Vol. VI, pp. 253-278, Plenum Press, New York (1984), which describes the use of expression vectors for plant cells, including, among others, PAPS2022, PAPS2023, and PAPS2034).

Suitable insect cells include cells and cell lines from *Bombyx*, *Trichoplusia* or *Spodotera* species. Baculovirus vectors available for expression of proteins in cultured insect cells (SF 9 cells) include the pAc series (Smith et al., Mol. Cell Biol. 3:2156-2165 (1983)) and the pVL series (Luckow, V. A., and Summers, M. D., Virology 170:31-39 (1989)).

Alternatively, the polypeptides disclosed herein may also be expressed in non-human transgenic animals such as rats, rabbits, sheep and pigs (Hammer et al. Nature 315:680-683 (1985); Palmiter et al. Science 222:809-814 (1983); Brinster et al. Proc. Natl. Acad. Sci. USA 82:4438-4442 (1985); Palmiter and Brinster Cell 41:343-345 (1985) and U.S. Pat. No. 4,736,866).

The polypeptides disclosed herein may also be prepared by chemical synthesis using techniques well known in the chemistry of proteins such as solid phase synthesis (Merrifield, J. Am. Chem. Assoc. 85:2149-2154 (1964); Frische et al., J. Pept. Sci. 2(4): 212-22 (1996)) or synthesis in homogenous solution (Houbenweyl, Methods of Organic Chemistry, ed. E. Wansch, Vol. 15 I and II, Thieme, Stuttgart (1987)).

Accordingly, there is provided a recombinant expression vector comprising an isolated nucleic acid molecule described herein. Further, there is provided a host cell comprising a nucleic acid or recombinant expression vector disclosed herein.

Multimers of scFv can also be formed by linking the two variable regions in vitro, for example, using chemical cross-linkers. For example, the regions may be coupled using heterobifunctional thiol-containing linkers as described in WO 90/10457, N-succinimidyl-3-(2-pyridyldithio-proprionate) or N-succinimidyl-5 thioacetate.

Methods and Uses:

The engineered scFvs provide a therapeutic antiviral drug that is useful for prevention and control of bovine respiratory disease (IBR) and bovine genital disease (IPV) via passive immunization.

Accordingly, there is provided a use of an effective amount of the scFv disclosed herein for the treatment of BHV-1 infection in cattle. The disclosure also includes a method of treating BHV-1 infection in cattle, comprising administering an effective amount of the scFv disclosed herein to a cow in need thereof. The disclosure also includes a use of the scFv disclosed herein in the preparation of a medicament for treating BHV-1 infection in cattle. The disclosure also includes a scFv disclosed herein for use in treating BHV1 infection in cattle.

As used herein, the phrase "effective amount" means an amount effective, at dosages and for periods of time necessary to achieve the desired result. Effective amounts of therapeutic may vary according to factors such as the disease state, age, sex, or weight of the animal. Dosage regime may be adjusted to provide the optimum therapeutic response. For example, several divided doses may be administered daily or the dose may be proportionally reduced as indicated by the exigencies of the therapeutic situation.

The term "treating" refers to treating and preventing BHV-1 infection and includes, without limitation, inhibiting viral replication, preventing viral entry into a cell, inhibiting viral spread and/or improving BHV-1-related symptoms.

In another aspect, there is provided a use of an effective amount of the scFv disclosed herein for neutralizing BHV-1 in cattle. The disclosure also includes a method of neutralizing BHV-1 in cattle, comprising administering an effective amount of the scFv disclosed herein to a cow in need thereof. The disclosure also includes a use of the scFv disclosed herein in the preparation of a medicament for neutralizing BHV-1 in cattle. The disclosure further includes a scFv disclosed herein for use in neutralizing BHV-1 in cattle. The neutralization is preferably in infected semen of the cow.

The term "neutralizing" refers to blocking the infective capacity of the virus. Non-limiting examples of neutralization include blocking the receptors on the cell or the virus or stopping the virus from replicating, for example, by lysis of the infected cells.

In a further embodiment, the methods and uses are for treating bovine respiratory disease (IBR) or bovine genital disease (IPV). In another embodiment, the methods and uses are for treating BHV-1 during transportation or parturition. In one embodiment, the treatment is via passive immunization. The scFv may be used or administered intranasally, intravaginally, by injection or mucosally. In another embodiment, scFv is used or administered in conjunction with conventional immunization, such as inactivated or modified live vaccines.

Compositions and Kits:

The application also provides compositions comprising the scFvs disclosed herein, with a pharmaceutically acceptable excipient, carrier, buffer or stabilizer.

The compositions described herein can be prepared by per se known methods for the preparation of pharmaceutically acceptable compositions that can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, 20th ed., Mack Publishing Company, Easton, Pa., USA, 2000). On this basis, the compositions include, albeit not exclusively, solutions of the substances in association with one or more pharmaceutically acceptable vehicles or diluents, and contained in buffered solutions with a suitable pH and iso-osmotic with the physiological fluids.

Pharmaceutical compositions include, without limitation, lyophilized powders or aqueous or non-aqueous sterile injectable solutions or suspensions, which may further contain antioxidants, buffers, bacteriostats and solutes that render the compositions substantially compatible with the tissues or the blood of an intended recipient. Other components that may be present in such compositions include water, surfactants (such as Tween), alcohols, polyols, glycerin and vegetable oils, for example. Extemporaneous injection solutions and suspensions may be prepared from sterile powders, granules, tablets, or concentrated solutions or suspensions. The scFv may be supplied, for example but not by way of limitation, as a lyophilized powder which is reconstituted with sterile water or saline prior to administration to the cow.

Pharmaceutical compositions may comprise a pharmaceutically acceptable carrier. Suitable pharmaceutically acceptable carriers include essentially chemically inert and non-toxic compositions that do not interfere with the effectiveness of the biological activity of the pharmaceutical composition. Examples of suitable pharmaceutical carriers include, but are not limited to, water, saline solutions, glycerol solutions, ethanol, N-(1(2,3-dioleyloxy)propyl)N,N,N-trimethylammonium chloride (DOTMA), diolesylphosphotidyl-ethanolamine (DOPE), and liposomes. Such compositions should contain a therapeutically effective amount of the compound, together with a suitable amount of carrier so as to provide the form for direct administration to the patient.

The composition may be in the form of a pharmaceutically acceptable salt which includes, without limitation, those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

In another aspect, there is provided a kit for treating or diagnosing bovine respiratory disease comprising an effective amount of the scFv described herein and directions for use thereof.

The kits disclosed herein can also include ancillary agents. For example, the kits can include instruments for injecting or applying the scFv or composition to a subject, such as a syringe; vessels for storing or transporting the scFv or composition; and/or pharmaceutically acceptable excipients, carriers, buffers or stabilizers. The kit may also comprise additional anti-BHV-1 agents and/or other medicinal agents.

Methods of Diagnosing, Diagnostic Agent and Diagnostic Kits

The scFvs disclosed herein also provide an immunodiagnostic reagent for detection of viral antigens, for example, in an immunoassay.

In one aspect, the disclosure provides a method of detecting BHV-1 infection in a cow comprising assaying a sample from the cow for binding with an scFv described herein, wherein binding by the scFv is indicative of the cow being infected with BHV-1.

The scFv described herein may also be used to detect whether a healthy cow has been vaccinated with a live vaccine for BHV-1. Accordingly, in an aspect, there is provided a method of determining whether a cow is vaccinated comprising assaying a sample from the cow for binding with an scFv described herein, wherein binding by the scFv is indicative of a vaccinated cow and lack of binding is indicative of an unvaccinated cow. In one embodiment, the sample is assayed by an immunoassay.

In another aspect, there is provided a diagnostic agent for use in the methods described above comprising (1) a scFv described herein that binds to a BHV-1 attached to (2) a label that produces a detectable signal, directly or indirectly. In one embodiment, the label is a radioisotope, such as $^3$H, $^{14}$C, $^{32}$P, $^{35}$S, $^{123}$I, $^{125}$I, $^{131}$I; a fluorescent or chemiluminescent compound, such as fluorescein isothiocyanate, rhodamine or luciferin; an enzyme, such as alkaline phosphatase, beta-galactosidase or horseradish peroxidase; an imaging agent or a metal ion. Methods of attaching a label to a protein, such as an scFv, are known in the art. In another embodiment, there is provided a kit comprising the diagnostic agent and instructions for use thereof.

The term "sample" as used herein refers to any fluid, cell or tissue sample from a cow which can be assayed for BHV-1.

The above disclosure generally describes the present disclosure. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

Construction of Functional Single Chain Fv with 7 Amino Acid Linker Against Bovine Herpes Virus Type-1 of Cattle scFv1-7L Results:

Design and Construction of Recombinant Single Chain Fv

An overlap PCR assay was developed (FIG. 1$i$) where the VJ and VDJ were individually amplified using primers with built-in SfiI sites as well as a seven codon overlapping flexible linker that permitted amplification of complete $V_\lambda$-linker-$V_H$ (FIG. 1$iia$, b, c). The recombinant $V_\lambda$-seven amino acid linker-$V_H$ was cloned into the SfiI cloning site of pPICZα expression vector that resulted in its expression under the control of strong AOX I promoter for high level heterologous protein production such that the in-built c-Myc and His-tag could be expressed. The nucleotide sequence was confirmed subsequent to cloning into pPICZα vector (FIG. 2). The P.

*pastoris* eukaryotic expression system has the advantages such as protein processing, folding and post-translational modifications with a higher heterologous protein production. The expression of AOX I gene is tightly regulated and induced by methanol to very high levels ($\geq 30\%$) of the total soluble protein in cells grown with methanol (Roggenkamp et al., 1984). The pPICZα vector was selected for secreted expression where zeocin resistance gene permits positive selection in *E. coli* and *P. pastoris*.

Expression and Purification of Recombinant scFv

First the recombinant plasmid pscFv1-7L was used to transform *E. coli* to obtain sufficient recombinant plasmid for transformation of *P. pastoris* (X-33) after its linearization. The transformed *P. pastoris*, both X-33 and KM71H strains, were grown in induction medium and the supernatant tested positive for the presence of recombinant protein at 72 h post induction. The presence of recombinant scFv was further confirmed in the supernatant using a sandwich ELISA 72 h post induction (data not shown). The recombinant protein was affinity purified and tested by electrophoresis and Western immunoblot. The recombinant scFv1-7L of approximately 30 kDa was noted in Coomassie stained 12% SDS-PAGE gel (FIG. 3a). Consistent with these observations a Western immunoblot also demonstrated recombinant scFv of identical molecular mass as expected for scFv1-7L under denaturing conditions (FIG. 3b). These observations suggested that $V_\lambda$-linker-$V_H$ configuration is expressed in *P. pastoris* consistent with theoretical expectation.

The Recombinant scFv Neutralize BHV-1 Virus

The recombinant scFvs are indeed functional as these inhibited >50% of 200 pfu BHV-1 infected MDBK cells in vitro (Table 1). Four independent sets of experiments demonstrated that recombinant scFv are capable of more than 50% plaque inhibition (Table 1) where scFv1-7L at a concentration as low as 3 µg/ml neutralized BHV-1 (FIG. 4). The presence of c-Myc epitope or 6× histidine tag and composition of soluble and flexible linker did not affect the virus neutralizing capability of the recombinant scFv. Further, these experiments demonstrated that $V_\lambda$-linker-$V_H$ configuration provided functional antigen recognition and viral neutralization ability.

Recombinant scFv1-7L Recognizes Viral Antigens in an Immunofluorescence Assay

The antigen recognition capability of the recombinant scFv-17L was tested in a mixture of virus infected and uninfected cells via indirect immunofluorescence. Similar to the parent IgG1 antibody against BHV-1 (FIG. 5b), the recombinant scFv-17L recognized viral antigens in the perinuclear and cytoplasmic region (FIG. 5c) of the virus infected MDBK cells. Thus, the recombinant scFv1-7L against BHV-1 retained the ability to specifically detect the viral antigens identical to the parent monoclonal IgG1 antibody against BHV-1 in an immunoassay.

scFv1-7L Material and Methods

Hybridoma

The mouse×cattle hetero-hybridoma alpha-BL5C2.870005 (HB-9907; U.S. Pat. No. 5,026,646) secreting anti-BHV-I IgG1 antibody was obtained from American Type Culture Collection (ATCC, Rockville, Md., USA) and grown in RPMI 1640 (GIBCO BRL, Gaithersburg, Md., USA) growth medium supplemented with 20% horse serum, 5 mM sodium pyruvate, 0.5 mM MEM non essential amino acids, 1 mM glutamine and 1% 100× antibiotic-antimycotic and (GIBCO BRL, Gaithersburg, Md., USA), 50 µM 2-mercaptoethanol (GIBCO BRL, Gaithersburg, Md., USA).

cDNA Synthesis and Overlap PCR Extension

Total cellular RNA was isolated from HB-9907 hybridoma cells using Trizol reagent (Invitrogen, Canada). The purity and concentration of RNA was estimated by spectrophotometry (Bio-Rad Smart Spec 3000, Bio-Rad, California, USA). First strand cDNA synthesis kit (Amersham Biosciences) was used for cDNA synthesis from total RNA. Briefly, 2.5 µg of RNA in 3 µl volume was denatured by incubation at 65° C. for 10 min and 1 µl of DTT, 1 µl of oligo-dT primer (25 ng) and 5 µl of first-strand reaction mixture containing murine leukemia reverse transcriptase were added and incubated at 37° C. for 1 h.

The rearranged VDJ gene was amplified using primers designed from the heavy chain FR-1 (PDHL; 5'GGTCAGTC-CTCTAGATCT TCCCAGGTGCAGCTGCG3' (SEQ ID NO:9)) and FR-4 (PDHRM; 5' CTGGCCGGCTTGGCCAC-TAGTGGAGGAGACGGTGACCAG 3' (SEQ ID NO:10)) with built in SfiI restriction sites. The PCR was performed with 1.5 mM MgCl$_2$, 0.8 µM each primer, 10 mM dNTPs and 2.5 U Taq polymerase. The conditions for PCR included a hot start followed by 30 cycles of denaturation at 95° C. for 1 min, annealing at 68° C. for 1 min and extension at 72° C. for 1 min followed by a final extension of 72° C. for 7 min. The VJ was amplified using primers designed from the light chain FR-1 (PDLLM; 5'GTGGCCCAGCCGGCCCAGGCTGTGCT-GACTCAG 3' (SEQ ID NO:11)) and FR-4 (PDLR; 5'GGAA-GATCTAGAGGACTGACCTAGGACGG TCAGTGTGGT 3' (SEQ ID NO:12)) with built in SfiI restriction sites. The reaction and cycle conditions for PCR were similar to those for VDJ amplification except for annealing at 64° C. The BLV10H8 (Saini et al., 1999) cDNA was used as a positive control in both VJ and VDJ amplifications. Following PCR amplification, both the VJ and VDJ products were subjected to gel electrophoresis and purified using the Qiaquick gel extraction kit (Qiagen Inc., USA).

The amplified VJ and VDJ products were combined in an overlap extension PCR (Horton et al., 1989) with a 7 amino acid linker (GQSSRSS (SEQ ID NO:1)) with PDLLM and PDHRM primers. The conditions for PCR included, initial denaturation at 94° C. for 30 s, followed by 30 cycles of denaturation at 94° C. for 2 min, annealing at 65° C. for 15 s, extension at 72° C. for 15 s and a final extension at 72° C. for 30 min. The overlap PCR product was gel purified using Qiaquick gel extraction kit (Qiagen Inc., USA) and was then cloned into pCR-TOPO-XL vector, (Invitrogen, Canada). The recombinant plasmids were isolated using Qiaprep plasmid isolation kit (Qiagen Inc. USA) and sequenced in both directions using M13 forward and reverse primers, by automated DNA sequencing (MOBIX lab, McMaster University, Hamilton, Ontario, Canada).

Cloning of $V_x$-seven Amino Acid Linker-$V_H$ in pPICZα Expression Vector

The recombinant plasmid with the overlap PCR product (p99070P2) was digested with SfiI enzyme, fractionated by gel electrophoresis and purified using Qiaquick gel extraction kit (Qiagen Inc., USA). The purified product was then ligated into dephosphorylated (Calf intestinal alkaline phosphatase, Roche, Canada) pPICZα expression vector (Invitrogen, Canada) and used to transform Top 10 *E. coli* (Invitrogen, Canada) by heat shock at 42° C. for 30 s. The transformed bacteria were plated on low salt LB agar plates containing 25 µg/ml zeocin. The zeocin resistant colonies were picked and inoculated into 2 ml low salt LB medium containing 25 µg/ml Zeocin. Plasmid DNA was isolated using Qiaprep plasmid isolation kit (Qiagen Inc. USA). The recombinant plasmid, pscFv1-7L, DNA was sequenced using 5'AOX1 and 3'AOX1 primers by automated DNA sequencing (MOBIX lab, McMaster University, Hamilton, Ontario, Canada).

Transformation of X-33 and KM71H *Pichia pastoris*

A single colony of X-33 *P. pastoris* strain was used to inoculate YPD medium and grown overnight at 30° C. on a shaker (250 rpm). The cells were diluted to an $OD_{600}$ of 0.1-0.2 in YPD medium and incubated for 4-6 h at 30° C. until the $OD_{600}$ reached 0.6-1.0. The cells were pelleted by centrifugation at 500 g for 5 min and resuspended in 10 ml of Solution 1 (sorbitol containing ethylene glycol and DMSO) and centrifuged at 500 g for 5 min. The cell pellet was again resuspended in 1 ml of Solution I and these competent cells were used for transformation. Easy comp transformation method (Easy Select, *Pichia* expression kit, Invitrogen, Canada) was used for transformation of X-33 and KM71H *P. pastoris* strains. For transformation, 50 µl of competent X-33 or KM71H cells were taken in a sterile microcentrifuge tube and 3 µg of SacI linearized recombinant plasmid was added. This was followed by addition of 1 ml of Solution II (PEG) to the DNA/cell mixture and the contents were mixed by vortexing the tube. The transformation reaction was then incubated at 30° C. in a water bath for 1 h and was mixed every 15 min. The cells were subjected to heat shock at 42° C. for 10 min and divided into two tubes with 525 µl each with 1 ml YPD medium added to each tube. The tube was incubated at 30° C. for 1 h followed by centrifugation at 3000 g for 5 min at 20° C. The cell pellet was resuspended in 150 µl of Solution III (salt solution). The entire transformation reaction was plated on YPDS agar plates containing 100 µg/ml zeocin and incubated at 30° C. for 3 days.

Induction of scFv Expression in X-33 and KM71H *Pichia pastoris* Strains

Single colonies of each of the 5 recombinant X-33 and KM71H *Pichia* were inoculated into buffered minimal glycerol (BMGY) medium. The cultures were grown at 30° C. on a shaker (250 rpm) for 16-18 h until $OD_{600}$ reached 2.0-6.0. The cells were harvested by centrifuging at 3000 g for 5 min. at 20° C. The cell pellet was resuspended to an $OD_{600}=1.0$ in 50 ml buffered minimal methanol (BMMY) medium to induce expression of scFv1-7L followed by incubation at 30° C. Methanol was added to the cells every 24 h to a final concentration of 0.5% in order to maintain induction. Supernatants collected from all the samples were analyzed for scFv secretion. The highest secreting clones were also tested in a sandwich ELISA using anti-Myc antibody (2.5 µg/ml) as the capture antibody and anti-His antibody coupled to alkaline phosphatase (1:2000) as the detecting antibody (Knott et al., 1998).

Purification of scFv1-7L

The secreted His-tagged scFv1-7L from recombinant X-33 *P. pastoris* was purified on a Ni-chelating resin column using the Probond purification system (Invitrogen, Canada). Briefly, the purification resin was poured into a 10 ml purification column and the resin was allowed to settle by gravity. The resin was washed twice with 6 ml of sterile distilled water. This was followed by adding 6 ml native binding buffer (50 mM $NaH_2PO_4$, 0.5 M NaCl, 10 mM imidazole). The resin was resuspended by inverting the column and allowed to settle. Recombinant X-33 *P. pastoris* supernatant containing scFv1-7L was applied to the column and allowed to bind for 30-60 min. The resin was allowed to settle by gravity and the supernatant aspirated. The column was washed four times with 8 ml of native wash buffer (50 mM $NaH_2PO_4$, 0.5 M NaCl, 20 mM imidazole). The His-tagged scFv1-7L was eluted in native elution buffer (50 mM $NaH_2PO_4$, 0.5 M NaCl, 250 mM imidazole). The eluted protein was dialyzed against PBS and analyzed by SDS-PAGE and Western blotting. Protein concentration was determined by Bio-Rad protein assay kit (Bio-Rad, California, USA).

SDS-PAGE and Western Immunoblot

Purified recombinant scFv-17L was fractionated on a 12% SDS-PAGE gel (Laemmli, 1970; Silva et al., 1995) and electrophoretically transferred onto nitrocellulose membranes (Schleicher and Schuell Inc. USA) in transfer buffer (25 mM Tris, 192 mM Glycine and 20% methanol). The membranes were washed and detected by anti-His antibody conjugated to alkaline phosphatase (1:2000; Invitrogen, Canada) for 1 h and immunodetection revealed by NBT-BCIP chromogen (Roche, Canada). In parallel, the scFv1-7L was observed via staining with Coomassie Blue (0.25% w/v, Coomassie Blue R-250 in 50:40:10 methanol:distilled water:glacial acetic acid).

Virus Neutralization Assay

The BHV-1 virus was initially titrated in Madin Darby bovine kidney cells (MDBK) using a plaque assay. The virus titre was determined to be $5 \times 10^7$ pfu/ml. Plaque reduction test was performed as described by Martin et al., (1999). Briefly, 100 pfu virus was mixed with 100 µl of different concentrations of purified scFv1-7L. The mixture was incubated at 20° C. for 1 h following which the MDBK cell monolayers were adsorbed with the virus alone or virus plus scFv mixtures for 1 h at 20° C. The monoclonal anti-BHV-1 IgG1 in the HB-9907 hybridoma supernatant was used as a positive control. The foetal bovine serum included in the medium also provided an in built heterologous antibody negative control, apart from bovine serum albumin (BSA), PBS and DMEM medium controls. The infected monolayers were washed three times with sterile PBS and overlaid with 0.7% agarose in DMEM growth medium containing 3% FBS. The cells were incubated at 37° C. for 4 days under 5% $CO_2$ atmosphere and fixed with 10% formalin. The cells were then stained with 0.75% crystal violet and the plaques counted and calculated on the basis of background non-specific inhibition by BSA. A minimum of 50% plaque reduction was considered positive for virus neutralization.

Indirect Immunofluorescence

A mixture of uninfected and BHV-1 infected MDBK cells (VMRD Inc. USA) were incubated with recombinant scFv-17L at the final concentration of 10 µg at 37° C. for 30 min. The cells were washed and stained with anti-myc antibody (1 µg; Invitrogen, Canada), followed by detection with Protein A conjugated to FITC (1 µg; Sigma-Aldrich, Canada). The cells were washed and examined under a fluorescence microscope (400×; Leica Microsystems Inc. IL, USA) at a wavelength of 495 nm.

scFv1-7L Discussion

The specificity enshrined in the antibody molecule has led to their tremendous use in immunodiagnostics but their therapeutic and clinical diagnostic potential (e.g., neutralization of toxins, radionuclide based imaging etc.) has been constrained by the need for species-specific reagents to avoid an undesired immune response, such as HAMA (human mouse antibodies). The advances in recombinant DNA technology and mammalian gene transfer techniques have provided alternative approaches for the generation of antibodies of desired specificity via synthetic recombinant antibodies e.g. scFv or Fab and development of transgenic mice, e.g humanized mouse (Lonberg et al., 1994; Green et al., 1994). The experiments disclosed herein led to the construction of functional recombinant scFv with a 7 amino acid linker against BHV-1. The necessity for the generation of scFv against BHV-1 is due to the fact that no effective vaccines are currently available for disease prevention. The modified live vaccines against BHV-1 currently being used do not permit disease eradication especially because of viral latency (Van Donkersgoed and Babuik, 1991; Van Donkersgoed and Klassen, 1995; Littlevan den Hurk, 2006). The passive immunization by a specific antibody against neutralizing epitope of BHV-1 provides an adjunct approach for disease prevention together with the vaccination, especially during stressful conditions when the latent virus may get activated. For these reasons, scFv against BHV-1 was developed that is capable of not only recognizing the viral antigen but also inhibiting viral replication in vitro.

The scFv1-7L construct was designed such that $V_\lambda$ and $V_H$, from an anti-BHV-1 monoclonal IgG1 antibody (HB-9907 hybridoma; Levings and Stoll, 1991), were linked via a soluble, flexible and protease resistant seven amino acid linker without any side chains that could possibly influence antigen binding function. The pPICZα vector permitted $V_\lambda$-linker-$V_H$ expression as fusion protein with in-built c-myc and 6×His-tag for use in subsequent purification or development of immunoassays. The $V_L$-$V_H$ configuration was preferred as it provided 5 to 10 Å greater bridging distance as compared to the corresponding $V_H$-$V_L$ bridging distance configuration (Huston et al., 1993; Borrebaeck, 1995). The P. pastoris system was chosen as it provides the advantages of higher eukaryotes with regard to protein processing and post-translational modifications and higher heterologous protein producing potential under the influence of AOX I promoter (Tschopp et al., 1987; Cregg et al., 1989; Cereghino et al., 2002). The P. pastoris has advantages over phage display system as it permits selection of positive clones without the panning step (Cregg et al., 1985; Daly and Hearn, 2005). The transformation of P. pastoris with the recombinant scFv1-7L construct led to secretion of scFv that could be purified by affinity chromatography for subsequent functional assays. The composition of the seven-amino acid linker or the presence of few additional residues of vector origin did not influence the antigen recognition capability of recombinant scFv1-7L. The seven amino acid linker used here does not disturb $V_L$-$V_H$ interface and provides a stable expression of scFv molecule. Indeed, the scFv1-7L could specifically recognize the BHV-1 in an immunofluorescence assay and also neutralize BHV-1 infected MDBK cells in vitro. Neither the linker used nor the additional components including c-myc and 6×His-tag caused any deleterious effect on the function of the recombinant scFv1-7L. Such characteristics of the recombinant scFv1-7L are consistent with the therapeutic and immunodiagnostic potential of similar recombinant proteins generated against toxins, viruses (Feng et al., 2003; Zhang et al., 2006) and cancer antigens (Desplanqc et al., 1994; Paoli et al., 2004; Cardinale et al., 2005; Donofrio et al., 2005; Padiolleau-Lefevre et al., 2007). The recombinant scFv1-7L with seven-amino acid linker expressed as scFv with a single antigen combining site is likely capable of forming diabodies by corresponding pairing between two scFv molecules. Further experiments such as X-ray crystallography aimed at determining the 3-dimensional structure of the scFv1-7L protein will be performed to determine such intermolecular dynamics of two identical scFvs at higher protein concentrations. Nevertheless, without wishing to be bound by any particular theory, a linker as short as seven amino acids is likely to favour diabody formation (Holliger et al., 1993; Atwell et al., 1999; Hudson and Kortt, 1999) and, thus, enhance avidity via bivalency.

The availability of recombinant scFv1-7L against BHV-1 provides a useful analytical reagent that may be used to identify the neutralizing B-cell epitope present on BHV-1 virus. Since BHV-1 is an alpha herpesvirus which is highly stable, the isolation of neutralizing B-cell epitope will help advance development of a subunit vaccine. Further, scFv provides a stable and homogeneous source of scFv1-7L for therapeutic and immunodiagnostic applications. The virus neutralization capability of the scFv in vitro is comparable to the parent monoclonal IgG1 antibody against BHV-1. In vivo virus challenge experiments under controlled laboratory and field conditions determine the efficacy of passive protection provided by the recombinant scFv1-7L. The parent monoclonal IgG1 antibody has been reported to significantly reduce mortality in rabbits experimentally infected with BHV-1 virus, as well as in in vitro experiments (Levings and Stoll, 1991). Further experiments test the ability of recombinant scFv1-7L to neutralize BHV-1 contamination of semen with an objective to break the transmission cycle of the virus. The fact that the recombinant scFv1-7L is capable of specifically recognizing viral antigens in an immunofluorescence assay provides opportunity for development of rapid and sensitive immunoassays for field applications. Thus, the recombinant scFv1-7L against BHV-1 provides a stable protease resistant scaffold with possible formation as diabody, which provides a virus specific therapeutic drug and diagnostic reagent.

In summary, the recombinant scFv1-7L against BHV-1 has been successfully produced that are functional and provide a therapeutic drug for prevention of BHV-1 infection in cattle via passive immunization. These recombinant scFvs also provide an immunodiagnostic reagent and a research tool for identification of neutralizing B-cell epitope on BHV-1 virus. These recombinant scFv should provide better tissue penetration due to their relatively low molecular size and are also likely less immunogenic as these correspond to the variable region alone of both heavy and light chain of an antibody. The availability of bovine scFv is unlikely to generate an immune response in cattle and, thus, should provide an ideal antiviral drug for in vivo and topical mucosal application. The availability of recombinant scFvs against BHV-1 together with MLV use is likely to prevent and help eradicate infectious bovine rhinotracheitis and infectious pustular vulvovaginitis in cattle, in addition to bovine respiratory disease complex. Further, these scFvs would permit immunodiagnosis, including differentiation of BHV-1 infected animals from those vaccinated against BHV-1.

Example 2

Construction of Single Chain Fv with 18 Amino Acids Against Bovine Herpes Virus Type-1

Example 2 scFv3-18L and scFv4m-18L Results

Construction of Recombinant scFv with 18 Amino Acid Linker

The strategy for synthesis of Vλ-linker-VH is outlined in FIG. 6(i), where the VDJ (FIG. 6iia) and VJ (FIG. 6iib) isolated from IgG1 secreting heterohybridoma against BHV-1 were co-amplified together with the nucleotide sequence encoding 18 amino acid linker (GQSSRSSGGGGSSGGGS (SEQ ID NO:4)). The overlap PCR product was cloned into Sfi I site of pPICZα vector (FIG. 7) that resulted in recombinant scFv fused with c-myc epitope and his-tag and expressed under the influence of AOX1 promoter. During cloning, one of the clones, pscFv4m-18L showed a nucleotide substitution from A to G (FIG. 8) leading to amino acid substitution (Asp89 by Gly89 in the FR3 region of the heavy chain). Both recombinant scFvs were analyzed for functional differences, if any, as a result of replacement mutation in the FR3 that could possibly influence antigen recognition.

Expression and Purification of Recombinant scFv with 18 Amino Acid Linker

The linearized pscFv3-18L and pscFv4m-18L recombinant plasmids were used to transform *P. pastoris* (KM71H strain) and grown in induction medium. The supernatant tested positive in an ELISA (data not shown) for secreted recombinant scFv3-18L and scFv4m-18L 72 h post induction using 0.5% methanol. The affinity-purified recombinant scFvs were tested by electrophoresis and Western immunoblot. Both the recombinant scFvs were observed to be approximately 30.5 kDa (FIG. 9a). The specificity of detection of recombinant scFv3-18L and scFv4m-18L is confirmed by detection in a Western immunoblot that also demonstrated recombinant scFvs of the expected 30.5 kDa (FIG. 9b). These observations confirm stable expression of both the recombinant scFv with the 18 amino acid linker in KM71H *P. pastoris*.

Recombinant scFvs with 18 Amino Acid Linker are Functional

Figure 10:
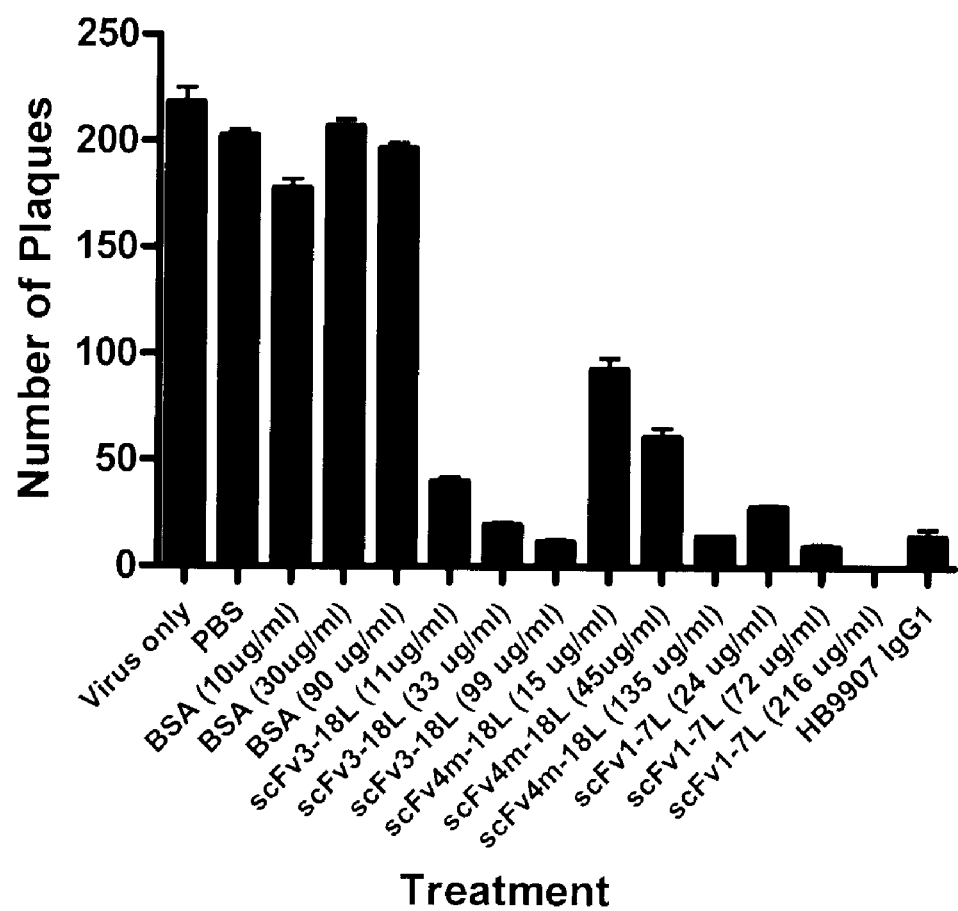

The functionality of recombinant scFv3-18L and scFv4m-18L was tested by a plaque reduction assay in BHV-1 infected MDBK cells grown in vitro. Four independent sets of experiments demonstrated >50% plaque inhibition (Table 2; FIG. 10ii) by recombinant scFv3-18L and scFv4m-18L at concentrations of 11 and 15 µg, respectively. These observations suggested that functionality of recombinant scFv4m-18L was not affected by a replacement mutation (Asp89 to Gly89) in FR3 as compared to scFv3-18L. Nevertheless, virus neutralization by the mutant scFv4m-18L differed in terms of its kinetics where 2.7- to 5-fold higher protein concentration was required for virus neutralization (FIG. 10i, ii) as compared to wild type scFv against BHV-1 with either 7 or 18 amino acid linker.

Figure 11:
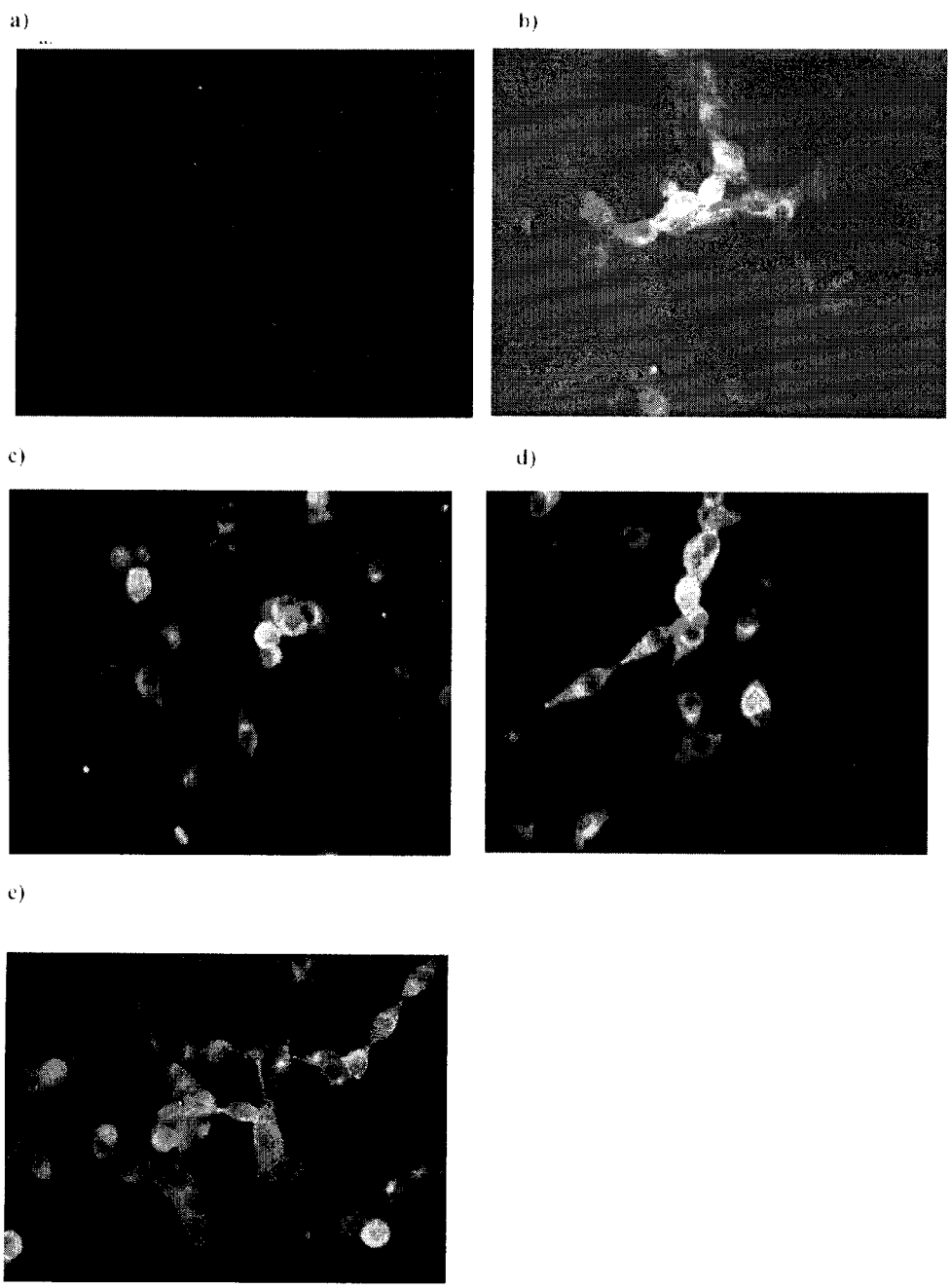

Consistent with virus neutralization capabilities of scFv3-18L and scFv4m-18L, these recombinant proteins specifically recognize viral antigens in BHV-1 infected MDBK cells (FIG. 11). These experiments provide unequivocal evidence that VJ-linker-VDJ orientation provides a functional configuration to antigen combining site that are capable of virus recognition and neutralization.

The Linker Size Does Not Affect Function of Recombinant scFvs Against BHV-1

A comparison of recombinant scFvs with seven and 18 amino acid linkers indicated that linker size neither affects their antigen recognition capability nor virus neutralization capacity as evidenced by an indirect immunofluorescence assay (FIG. 11) and virus neutralization kinetics (FIG. 10i and ii). By contrast, a single nucleotide replacement mutation in the FR3 can influence the viral neutralization kinetics (FIG. 10b) without affecting the antigen recognition ability (FIG. 11). While scFv1-7L could form diabodies given the linker size and scFv with 18 amino acid linker could only be expressed as monomer scFv, 50% viral neutralization end points are comparable among the two recombinant proteins (scFv3-18L, 5.5 µg/ml; scFv1-7L, 3 µg/ml). This is in contrast to scFv4m-18L where a single nucleotide replacement mutation dramatically changes the virus neutralization kinetics and end point of 50% viral neutralization is achieved by a high concentration (15 µg/ml) of the recombinant protein. Overall, these experiments demonstrate that linker size does not affect recombinant bovine scFvs directed against neutralizing B cell epitope present on BHV-1 virus.

Example 2 scFv3-18L and scFv4m-18L Materials and Methods

Hybridoma

The mouse×cattle hetero-hybridoma alpha-BL5C2.870005 (HB-9907; U.S. Pat. No. 5,026,646) secreting anti-bovine herpesvirus Type- (BHV-1) IgG1 antibody, was obtained from American Type Culture Collection (ATCC, Rockville, Md., USA) and grown in RPMI 1640 (GIBCO BRL, Gaithersburg, Md., USA) growth medium supplemented with 20% horse serum, 5 mM sodium pyruvate, 0.5 mM MEM non essential amino acids, 1 mM glutamine and 1% 100× antibiotic-antimycotic (GIBCO BRL, Gaithersburg, Md., USA) and $5 \times 10^{-5}$ M 2-mercaptoethanol (GIBCO BRL, Gaithersburg, Md., USA).

cDNA Synthesis and Overlap PCR

Total cellular RNA was isolated from HB-9907 hybridoma cells using Trizol reagent (Invitrogen, Canada) and concentration of RNA was estimated by spectrophotometry (Biorad Smartspec 3000, Bio-rad, California, USA). First strand cDNA synthesis kit (Amersham Biosciences) was used for cDNA synthesis from total cellular RNA. Briefly, 2.5 µg of total RNA was diluted in 3 µl volume of RNase free water and denatured by incubation at 65° C. for 10 min. To this, 1 µl of DTT, 1 µl of oligo-dT primer (25 ng) and 5 µl of first strand reaction mixture containing murine leukemia reverse transcriptase, were added followed by incubation at 37° C. for 1 h.

The cDNA was amplified for rearranged heavy (VDJ) and light chain (VJ) variable region genes. The VDJ was amplified using primers designed from the heavy chain FR1 (PDHL18; 5'GGTCAGTCCTCTAGATCTTCCGGCGGTG-GTGGCAGCTCCGGTGGTGG CGGTTCCCAGGTG-CAGCTGCG 3' (SEQ ID NO:13)) and FR4 (PDHRM; 5' CTGGCCGGCTTGGCCACTAGTGGAG-GAGACGGTGACCAG 3' (SEQ ID NO:14)) with built in SfiI restriction sites. The PCR was performed with 1.5 mM $MgCl_2$, 0.8 µM each primer, 10 mM dNTPs and 2.5 U Taq polymerase. The PCR conditions included a hot start followed by 30 cycles of denaturation at 95° C. for 1 min, annealing at 68° C. for 1 min and extension at 72° C. for 1 min with a final extension of 72° C. for 7 min. The VJ was amplified using primers designed from the light chain FR1 (PDLLM; 5'GTGGCCCAGCCGGCCCAGGCTGTGCT-GACTCAG 3' (SEQ ID NO:15)) and FR4 (PDLR; 5'GGAA-GATCTAGAGGACTGACCTAGGACGGTCAGTG TGGT 3' (SEQ ID NO:16)) with built-in SfiI restriction sites. The PCR conditions were similar to those for VDJ amplification except for the annealing temperature of 68° C. The cDNA synthesized from total RNA isolated from BLV10H8 hybridoma (Saini et al., 1999) was used as positive control in VJ and VDJ amplification. The purified VJ and VDJ PCR products (Qiaquick gel extraction kit; Qiagen Inc., USA) were combined in an overlap extension PCR using an 18 amino acid linker (GQSSRSSSGGGSSGGGGS (SEQ ID NO:4)) using primers from FR1 of VJ and FR4 of VDJ. The conditions for PCR included, denaturation at 94° C. for 30 s, 30 cycles of 94° C. for 2 min, annealing at 65° C. for 15 s, extension at 72° C. for 15 s, followed by a final extension at 72° C. for 30 min. The overlap PCR product was purified using Qiaquick gel extraction kit (Qiagen Inc., USA) and cloned in pCR-TOPO-XL vector (Invitrogen, Canada). The ligate was used to transform Top 10 *E. coli* cells (Invitrogen, Canada). Recombinant plasmids were isolated using a silicon column (Qia plasmid extraction kit, Qiagen Inc., USA) and sequenced using M13 forward and reverse primers by automated DNA sequencing (MOBIX lab, McMaster University, Hamilton, Ontario, Canada).

Cloning of $V_x$-18 Amino Acid Linker-$V_H$ in pPICZα Vector

The recombinant plasmids with $V_\lambda$-linker-$V_H$ (p99070P18L-4; and p99070P18L-3 with mutation in FR3) were digested with SfiI enzyme and gel purified using Qiaquick gel extraction kit (Qiagen Inc., USA). The purified $V_x$-linker-$V_H$ product was then ligated into dephosphorylated (Calf intestinal alkaline phosphatase, Roche, Canada) pPICZα expression vector (Invitrogen, Canada). The ligate was used to transform Top 10 E. coli (Invitrogen, Canada) by heat shock at 42° C. for 30 s. Recombinant plasmids', pScFv3-18L and pscFv4m-18L, DNA was isolated from transformed E. coli (Qia prep plasmid isolation kit, Qiagen Inc. USA) and were sequenced using 5'AOX1 and 3'AOX1 primers by automated DNA sequencing (MOBIX lab, McMaster University, Hamilton, Ontario, Canada).

Transformation of KM71H Pichia pastoris

A single colony of KM71H P. pastoris strain was used to inoculate 10 ml YPD medium and the yeast grown overnight at 30° C. on a shaker (250 rpm). Following overnight growth, the cells were diluted to an $OD_{600}$ of 0.1-0.2 in 10 ml of YPD medium and incubated for 4-6 h at 30° C. until the $OD_{600}$ reached 0.6-1.0. The cells were pelleted by centrifugation at 500 g for 5 min and resuspended in 10 ml of Solution 1 (sorbitol containing ethylene glycol and DMSO) and centrifuged at 500 g for 5 min. The cell pellet was resuspended in 1 ml of Solution I and these competent cells were used for transformation.

Easy comp transformation method (Easy Select, Pichia expression kit, Invitrogen, Canada) was used for transformation of KM71H P. pastoris strain. Approximately, 10 µg of the plasmid DNA was linearized by restriction enzyme digestion with SacI enzyme. For transformation, 50 µl of competent KM71H P. pastoris cells were taken in a sterile microcentrifuge tube and 3 µg of linearized recombinant expression vector DNA was added to the cells. This was followed by addition of 1 ml of Solution II (PEG) to the DNA/cell mixture and the contents were mixed. The transformation reaction was then incubated at 30° C. in a water bath for 1 h and was mixed every 15 min during the incubation. The cells were subjected to heat shock at 42° C. for 10 min. The cells were split into two tubes with 525 µl each and 1 ml YPD medium added to each tube followed by incubation at 30° C. for 1 h. The cells were centrifuged at 3000 g for 5 min at 20° C. and resuspended in 150 µl of Solution III (salt solution). The entire transformation reaction was plated on YPDS agar plates containing 100 µg/ml Zeocin and incubated at 30° C. for 3 days.

Induction and Expression of scFvs in KM71H Pichia pastoris

Single colonies from each recombinant KM71H P. pastoris were inoculated into buffered minimal glycerol (BMGY) medium. The cultures were grown at 30° C. on a shaker (250 rpm) for 16-18 h until the $OD_{600}$ reached 2-6. The cells were harvested by centrifuging at 3000 g for 5 min at 20° C. The cell pellet was resuspended to an $OD_{600}$=1.0 in buffered minimal methanol (BMMY) medium to induce expression of scFv3-18L and scFv4m-18L followed by incubation at 30° C. Methanol was added to the cells every 24 h to a final concentration of 0.5% in order to maintain induction. Supernatants were collected and tested for secretion of scFv in the medium. The highest secreting clones were also tested in a sandwich ELISA using anti-myc antibody (2.5 µg/ml) as the capture antibody and anti-Histag antibody coupled to alkaline phosphatase (0.1 to 0.2 µg or 1:2000; Invitrogen, Canada) for immunodetection.

Purification of scFv

The secreted His-tagged scFv was purified on a Ni-NTA column using the Probond purification system (Invitrogen, Canada). The protein was purified under native conditions to preserve its activity. Briefly, the purification resin was poured into a 10 ml purification column and was allowed to settle by gravity. The resin was washed twice with 6 ml of sterile distilled water. This was followed by addition of 6 ml native binding buffer. The resin was resuspended by inverting the column and allowed to settle by gravity. Eight ml of recombinant KM71H P. pastoris supernatant containing scFv were applied to the column and allowed to bind for 30-60 min. The column was washed four times with 8 ml of native wash buffer (50 mM $NaH_2PO_4$, 0.5 M NaCl, 20 mM imidazole). The His-tagged scFv was eluted with 8 ml of native elution buffer (50 mM $NaH_2PO_4$, 0.5 M NaCl, 250 mM imidazole). The eluted protein was dialyzed against PBS and protein concentration estimated by Bio-rad protein assay kit (Bio-Rad, California, USA).

SDS-PAGE and Western Immunoblot

Purified recombinant scFv3-18L and scFv4m-18L were electrophored on a 12% SDS-PAGE gel (Laemmli, 1970; Silva et al., 1995) and transferred onto nitrocellulose membranes (Schleicher and Schuell Inc. USA) via electrophoresis in transfer buffer (25 mM Tris, 192 mM Glycine and 20% methanol). The membranes were washed and detected by anti-His antibody conjugated to alkaline phosphatase (1:2000; Invitrogen, Canada) for 1 h and immunodetection revealed by NBT-BCIP chromogen (Roche, Canada). In parallel, the scFv3-18L and scFv4m-18L proteins were observed by coomassie blue staining (0.25% w/v, Coomassie Blue R-250 in 50:40:10 methanol:distilled water:glacial acetic acid).

Virus Neutralization Assay

The neutralizing ability of recombinant scFv3-18L and scFv4m-18L was tested using plaque reduction assay. The BHV-1 virus was initially titrated in Madin Darby bovine kidney cells (MDBK) using plaque assay. The virus titre was determined to be $5 \times 10^7$ pfu/ml. Plaque reduction test was performed as described by Martin et al., (1999). Breifly, 100 pfu virus was mixed with 100 µl of different concentrations of purified scFv3-18L and scFv4m-18L and incubated at 20° C. for 1 h following which the MDBK cell monolayers were allowed to adsorb with the virus alone or virus plus scFv mixtures for 1 h at 20° C. The HB-9907 hybridoma supernatant containing monoclonal anti-BHV-1 IgG1 was used as a positive control. The foetal bovine serum included in the medium provided a built-in heterologous antibody negative control, apart from bovine serum albumin (BSA), PBS and DMEM medium controls. The infected monolayers were washed three times with sterile PBS and overlaid with 0.7% agarose in DMEM growth medium containing 3% FBS. The cells were incubated at 37° C. for 4 days under 5% $CO_2$ atmosphere and fixed with 10% formalin. The cells were then stained with 0.75% crystal violet and resulting plaques were counted and calculated on the basis of non-specific inhibition by BSA. A minimum of 50% plaque reduction was considered positive for virus neutralization activity.

Indirect Immunofluoresence

A mixture of uninfected and infected BHV-1 MDBK cells (VMRD Inc. USA) were incubated with recombinant scFv3-18L and scFv4m-18L at the final concentration of 10 µg at 37° C. for 30 min. The cells were washed and stained with anti-Myc antibody (1 µg; Invitogen, Canada), followed by detection with Protein A conjugated to FITC (1 µg; Sigma-Aldrich, Canada). The cells were washed and examined under a fluorescence microscope (400×; Leica Microsystems Inc., IL, USA) at a wavelength of 495 nm.

Example 2 scFv3-18L and scFv4m-18L Discussion

For the development of clinically relevant therapeutic antibodies, animal immunization and subsequent humanization for use in human subjects has been the conventional approach (Rader et al., 2000). The availability of recombinant DNA techniques for constructing and expressing minimal antigen binding fragments or whole immunoglobulin molecules (Carter, 2006) in microbial systems such as yeast (Boder and Wittrup, 1997) provides a powerful tool for developing species-specific antibodies of the desired affinity. The development of such therapeutic recombinant antibodies or their derivatives may eliminate the side effects associated with heterologous antigens, e.g. HAMA response upon injection of murine antibodies into humans. The experiments outlined here have led to the construction of single chain Fv with 18-amino acid linkers that would enforce this molecule to exist as single-chain Fv with a monomeric antigen combining site where multimerization cannot occur. The bovine recombinant scFv with an 18-amino acid linker is functional since it is capable of neutralizing BHV-1 virus similar to the parent monoclonal IgG1 antibody against BHV-1 (Levings and Stoll, 1991) and, also, recombinant scFv with a seven-amino acid linker (Koti, 2007). Further, these scFv with longer linker size recognize viral antigens by indirect immunofluorescence similar to the parent monoclonal IgG1 antibody or its another derivative scFv with seven amino acid linker. Since recombinant scFv with seven-amino acid linker could multimerize to form diabody unlike scFv with 18-amino acid linker that could only form a monomeric antigen combining site, similar binding and functional characteristics of both the recombinant proteins suggests that either form is functionally relevant. Nevertheless, molecular modeling and structural configuration by X-ray crystallography or NMR is required to determine if scFv with seven-amino acid linker is indeed present in a configuration that these could multimerize. Alternatively, it could be argued that the presence of scFv either as monomeric or dimeric form is not relevant in the context of antigen recognition or virus neutralization function since light chains contribute lithe to antigen binding function (Sinclair et al., 1995b) or may provide only a supporting platform (Saini et al., 2003). This would essentially mean that variable heavy region alone is involved in antigen recognition but this would require further experimentation where such antibody functions need to be analyzed by expressing $V_H$ and domains individually. The availability of functional recombinant scFv against BHV-1 in monomeric and bivalent form is important from pharmacokinetic point of view where monomeric form would have better tissue penetration and blood clearance in vivo as compared to bivalent diabody (Colcher et al., 1990). The covalent complexes of scFv are, in general, preferred due to superior intrinsic stability (Fitzgerald et al., 1997; Cochlovius et al., 2000; Olafson et al., 2004)

The linker size and composition influences the function of recombinant scFv as these provide different levels of aggregation and may alter the interface of $V_L$-$V_H$ configuration (Dalaqua, 1998; Turner et al., 1997). Often, the Fv domains are stabilized through a 15-amino acid long flexible and hydrophilic linker composed of three repeats $(Gly_4Ser)_3$ (Huston et al, 1988) where a smaller size (less than 12 amino acids) is preferred for non-covalent scFv multimerization (Korrt et al., 1997; Arndt et al., 1998; Atwell et al., 1999). The properties such as $V_H$-$V_L$ interface stability, concentration, ionic strength etc can influence multimerization into diabodies or higher multimers (Desplancq et al., 1994; Arndt et al., 1998). A modified linker composition that has glutamine with a higher monoisotopic mass as compared to glycine and serine in both seven and 18 amino acid linkers, has been used in the expression of both the recombinant scFvs against BHV-1. Such a linker modification does not affect antigen recognition or virus neutralization function of the recombinant scFvs with a linker size of either 7 or 18 amino acids. Similarly, the linker size that may or may not cause multimerization, does not affect the virus neutralization and antigen recognition function. The experiments demonstrating end point for virus neutralizaiton are comparable between recombinant scFvs with seven and 18 amino acid linkers where >50% plaque reduction is achieved by 3 and 5.5 µg/ml recombinant protein, respectively. This suggests that recombinant scFv originating from bovine IgG1 antibody against BHV-1, whether present in monovalent or bivalent form are effectively functional. Further, these experiments provide evidence that these two linker sizes do not seem to affect expression of scFv in *P. pastoris* as these do not mask or interact with critical residues either on the surface of scFv or on an intermediate species during protein refolding. Such influences of the linker size are, however, difficult to predict without the knowledge of the 3-dimensional structure of the recombinant proteins in question.

A single nucleotide mutation that resulted in replacement from aspartic acid to glycine in the FR3 region at position 89 in the heavy chain was serendipitously isolated in one of the recombinant scFvs during cloning. Since the secretion of scFv can be enhanced by such mutations or this could also influence the aggregation of a folding intermediate (Knappik and Pluckthun, 1995) that could influence antigen binding properties, the mutant scFv with 18 amino acid linker was analyzed for its functional properties. The BHV-1 antigen recognition by the mutant scFv with 18 amino acid linker was comparable to recombinant scFv with 18 amino acid linker and the parent monoclonal IgG1 antibody against BHV-1, known to significantly reduce mortality in rabbits experimentally infected with BHV-1 and in in vitro experiments (Levings and Stoll, 1991). Thus, a single replacement mutation in the FR3 did not affect antigen binding per se. Nevertheless, the mutation from Asp89 to Gly89 did influence the viral neutralization kinetics where neutralization end point was achieved by 2.7 to 5-fold higher recombinant protein concentration. These observations suggest that the FR3 residues might subtly influence the function of recombinant scFvs in the context of intrinsic configurational variation that changes antigen binding dynamics. The X-ray crystallographic studies are required to understand such subtle differences in the composition of FR regions that may not affect antigen recognition but can influence functional outcome. This might be related to minor differences in the affinity or the configurational variation or stability during antigen-antibody interaction in the context of viral neutralization. Further studies are required to determine if the secretion of mutant scFv was enhanced or decreased as observed earlier with mutations in two FR residues that influenced the aggregation of a folding intermediate and toxicity to the bacteria (Knappic and Pluckthun, 1995).

In summary, the experimental evidence suggests that recombinant scFvs, either monovalent (scFv) or bivalent (diabody), are effectively capable of antigen recognition and virus neutralization. Further, any substitution resulting in replacement mutation in FR composition, especially FR3, may have subtle influence on either the affinity or functional dynamics relevant to therapeutic significance. Future studies should aim at evaluating therapeutic potential of recombinant scFvs by in vivo virus challenge experiments under laboratory and field conditions for sustained protection against BHV-1 infection in cattle.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE I

Neutralization of BHV-1 virus by recombinant scFv1-7L protein

| Treatment | Percent plaque reduction | |
|---|---|---|
| | Experiment I | Experiment II |
| Virus alone* | 0 | 0 |
| Phosphate buffered saline* | 0 | 0 |
| Bovine serum albumin** | | |
| 10 μg/ml | NA | NA |
| 30 μg/ml | NA | NA |
| 90 μg/ml | NA | NA |
| Anti-BHV-1 IgG1 antibody (hybridoma supernatant) | | |
| Undiluted | 90.86 | 94.21 |
| 1:10 diluted | 82.23 | 81.08 |
| scFv1-7L | | |
| 24 μg/ml | 86.29 | 84.76 |
| 72 μg/ml | 95.93 | 94.21 |
| 216 μg/ml | 100 | 100 |

*Cooper strain of BHV-I (200 pfu) was used for plaque reduction assay;
**percent plaque reduction was calculated on the basis of non-specific inhibition by heterologous protein BSA. These data are consistent with similar results obtained from a total of four independent experiments.

TABLE 2

Neutralization of BHV-1 virus by recombinant scFv3-18L and scFv4m-18L proteins

| Treatment | Percent Plaque reduction | |
|---|---|---|
| | Experiment I | Experiment II |
| Virus alone* | 0 | 0 |
| Phosphate buffered saline* | 0 | 0 |
| Bovine serum albumin** | | |
| 10 μg/ml | NA | NA |
| 30 μg/ml | NA | NA |
| 90 μg/ml | NA | NA |
| Anti BHV-1 IgG1 antibody (hybridoma supernatant) | | |
| Undiluted | 90.86 | 94.21 |
| 1:10 diluted | 82.23 | 81.08 |
| scFv3-18L | | |
| 11 μg/ml | 78.68 | 80.03 |
| 33 μg/ml | 89.34 | 90.54 |
| 99 μg/ml | 93.40 | 94.74 |
| scFv4m-18L | | |
| 15 μg/ml | 55.83 | 48.50 |
| 45 μg/ml | 67.00 | 70.04 |
| 135 μg/ml | 92.38 | 92.64 |

*Cooper strain of BHV-I (200 pfu) was used to infect MDBK cells for plaque reduction assay;
**percent plaque reduction was calculated on the basis of non-specific inhibition by heterologous protein BSA. These data are consistent with similar results obtained from a total of four independent experiments.

REFERENCES

Arndt, K. M., K. M. Muller, and A. Pluckthun. 1998. Factors influencing the dimer to monomer transition of an antibody single-chain Fv fragment. *Biochemistry* 37: 12918-12926

Atwell, J. L., K. A. Breheney, L. J. Lawrence, A. J. McCoy, A. A. Kortt, and P. J. Hudson. 1999. scFv multimers of the anti-neuraminidase antibody NC10: length of the linker between VH and VL domains dictates precisely the transition between diabodies and triabodies. *Protein Eng.* 12: 597-604

Bird, R. E., K. D. Hardman, J. W. Jacobson, S. Johnson, B. M. Kaufman, S. M. Lee, T. Lee, S. H. Pope, G. S. Riordan, and M. Whitlow. 1988. Single-chain antigen-binding proteins. *Science* 242: 423-426

Boder, E. T. and K. D. Wittrup. 1997. Yeast surface display for screening combinatorial polypeptide libraries. *Nat. Biotechnol.* 15: 553-557

Borrebaeck, C. A. 1994. Antibody engineering. $2^{nd}$ Edition. Oxford University Press, USA.

Boulianne, G. L., N. Hozumi, and M. J. Shulman. 1984. Production of functional chimaeric mouse/human antibody. *Nature* 312: 643-646

Brinkmann, U., P. S. Chowdhury, D. M. Roscoe, and I. Pastan. 1995. Phage display of disulfide-stabilized Fv fragments. *J. Immunol. Methods* 182: 41-50

Feng J, Xie Z, Guo N, Shen B. 2003. Design and assembly of anti-CD16 ScFv antibody with two different linker peptides. J Immunol Methods. 282:33-43.

Cardinale, A., I. Filesi, V. Vetrugno, M. Pocchiari, M. S. Sy, and S. Biocca. 2005. Trapping prion protein in the endoplasmic reticulum impairs PrPC maturation and prevents PrPSc accumulation. *J. Biol. Chem.* 280: 685-694

Carter, P. 2001. Improving the efficacy of antibody-based cancer therapies. *Nat. Rev. Cancer.* 1: 118-129

Carter, P. J. 2006. Potent antibody therapeutics by design. *Nat. Rev. Immunol.* 6: 343-357

Cereghino, G. P., J. L. Cereghino, C. Ilgen, and J. M. Cregg. 2002. Production of recombinant proteins in fermenter cultures of the yeast *Pichia pastoris*. *Curr. Opin. Biotechnol.* 13: 329-332.

Cochlovius, B., S. M. Kipriyanov, M. J. Stassar, J. Schuhmacher, A. Benner, G. Moldenhauer, and M. Little. 2000. Cure of Burkitt's lymphoma in severe combined immunodeficiency mice by T cells, tetravalent CD3×CD19 tandem diabody, and CD28 costimulation. *Cancer Res.* 60: 4336-4341

Colcher, D., R. Bird, M. Roselli, K. D. Hardman, S. Johnson, S. Pope, S. W. Dodd, M. W. Pantoliano, D. E. Milenic, and J. Schlom. 1990. In vivo tumor targeting of a recombinant single-chain antigen-binding protein. *J. Natl. Cancer Inst.* 82: 1191-1197.

Cregg, J. M., K. J. Barringer, A. Y. Hessler, and K. R. Madden. 1985. *Pichia pastoris* as a host system for transformations. *Mol. Cell. Biol.* 5: 3376-3385

Cregg, J. M., K. R. Madden, K. J. Barringer, G. P. Thill, and C. A. Stillman. 1989. Functional characterization of the two alcohol oxidase genes from the yeast *Pichia pastoris*. *Mol. Cell. Biol.* 9: 1316-1323

Dall'Acqua, W. and P. Carter. 1998. Antibody engineering. *Curr. Opin. Struct. Biol.* 8: 443-450.

Daly, R. and M. T. Hearn. 2005. Expression of heterologous proteins in *Pichia pastoris*: a useful experimental tool in protein engineering and production. *J. Mol. Recognit.* 18: 119-138

Desplancq, D., D. J. King, A. D. Lawson, and A. Mountain. 1994.

Multimerization behaviour of single chain Fv variants for the tumour-binding antibody B72.3. *Protein Eng.* 7: 1027-1033

Donofrio, G., F. L. Heppner, M. Polymenidou, C. Musahl, and A. Aguzzi. 2005. Paracrine inhibition of prion propagation by anti-PrP single-chain Fv miniantibodies. *J. Virol.* 79: 8330-8338

FitzGerald, K., P. Holliger, and G. Winter. 1997. Improved tumour targeting by disulphide stabilized diabodies expressed in *Pichia pastoris*. *Protein Eng.* 10: 1221-1225

Gibbs, E. P. J and M. M. Rweyemamy. 1977. Bovine herpesviruses, Part I. Bovine herpesvirus 1. *Vet. Bull.* 47: 317-320

Green, L. L., M. C. Hardy, C. E. Maynard-Currie, H. Tsuda, D. M. Louie, M. J. Mendez, H. Abderrahim, M. Noguchi, D. H. Smith, and Y. Zeng. 1994. Antigenspecific human monoclonal antibodies from mice engineered with human Ig heavy and light chain YACs. *Nat. Genet.* 7: 13-21)

Harvey, B. R., G. Georgiou, A. Hayhurst, K. J. Jeong, B. L. Iverson, and G. K. Rogers. 2004. Anchored periplasmic expression, a versatile technology for the isolation of high-affinity antibodies from *Escherichia coli*-expressed libraries. *Proc. Natl. Acad. Sci. U.S.A.* 101: 9193-9198

Holliger, P., T. Prospero, and G. Winter. 1993. "Diabodies": small bivalent and bispecific antibody fragments. *Proc. Natl. Acad. Sci. U.S.A.* 90: 6444-6448

Hudson, P. J. and A. A. Kortt. 1999. High avidity scFv multimers; diabodies and triabodies. *J. Immunol. Methods* 231: 177-189.

Huston, J. S., D. Levinson, M. Mudgett-Hunter, M. S. Tai, J. Novotny, M. N. Margolies, R. J. Ridge, R. E. Bruccoleri, E. Haber, and R. Crea. 1988. Protein engineering of antibody binding sites: recovery of specific activity in an anti-digoxin single-chain Fv analogue produced in *Escherichia coli*.Proc. Natl. Acad. Sci. U.S.A. 85: 5879-5883

Huston, J. S., M. S. Tai, J. McCartney, P. Keck, and H. Oppermann. 1993. Antigen recognition and targeted delivery by the single-chain Fv. *Cell Biophys.* 22: 189-224

Jones, C. 2003. Herpes simplex virus type 1 and bovine herpesvirus 1 latency. *Clin. Microbiol. Rev.* 16: 79-95

Jones, C. 1998. Alphaherpesvirus latency: its role in disease and survival of the virus in nature. *Adv. Virus Res.* 51: 81-133.

Jones, C., Chowdhury, S., 2007, A review of the biology of bovine herpesvirus type 1 (BHV-1), its role as a cofactor in the bovine respiratory disease complex and development of improved vaccines. *Anim. Health. Res. Rev.* 8:187-205

Knappik, A. and A. Pluckthun. 1995. Engineered turns of a recombinant antibody improve its in vivo folding. *Protein Eng.* 8: 81-89

Knott, J., C. Bona, and A. Kaushik. 1998. The primary antibody repertoire of kappadeficient mice is characterized by non-stochastic Vlamda1+V(H) gene family pairings and a higher degree of self-reactivity. *Scand. J. Immunol.* 48: 65-72)

Kohler, G. and C. Milstein. 1975. Continuous cultures of fused cells secreting antibody of predefined specificity. *Nature* 256: 495-497

Kortt, A. A., M. Lah, G. W. Oddie, C. L. Gruen, J. E. Burns, L. A. Pearce, J. L. Atwell, A. J. McCoy, G. J. Howlett, D. W. Metzger, R. G. Webster, and P. J. Hudson. 1997. Single-chain Fv fragments of anti-neuraminidase antibody NC10 containing five- and ten-residue linkers form dimers and with zero-residue linker a trimer. *Protein Eng.* 10: 423-433)

Koti M., 2007. Immunogenetics of bovine antibody diversity and construction of recombinant therapeutic antibody. PhD thesis. University of Guelph, Guelph, Ontario, Canada.

Laemmli, U. K. 1970. Cleavage of structural proteins during the assembly of the head of bacteriophage T4. Nature 227: 680-685)

Levings, R. L. & Stoll, I. R. 1991. U.S. Pat. No. 5,026,646.

Lonberg, N., L. D. Taylor, F. A. Harding, M. Trounstine, K. M. Higgins, S. R. Schramm, C. C. Kuo, R. Mashayekh, K. Wymore, and J. G. McCabe. 1994. Antigenspecific human antibodies from mice comprising four distinct genetic modifications. *Nature* 368: 856-859)

Martin, S. W., E. Nagy, D. Armstrong, and S. Rosendal. 1999. The associations of viral and mycoplasmal antibody titers with respiratory disease and weight gain in feedlot calves. *Can. Vet. J.* 40: 560-7, 570

Maynard, J. and G. Georgiou. 2000. Antibody engineering. *Annu. Rev. Biomed. Eng.* 2: 339-376.

Morrison, S. L., M. J. Johnson, L. A. Herzenberg, and V. T. Oi. 1984. Chimeric human antibody molecules: mouse antigen-binding domains with human constant region domains. *Proc. Natl. Acad. Sci. U.S.A.* 81: 6851-6855

Olafsen, T., C. W. Cheung, P. J. Yazaki, L. Li, G. Sundaresan, S. S. Gambhir, M. A. Sherman, L. E. Williams, J. E. Shively, A. A. Raubitschek, and A. M. Wu. 2004. Covalent disulfide-linked anti-CEA diabody allows site-specific conjugation and radiolabeling for tumor targeting applications. *Protein Eng. Des. Sel.* 17: 21-27)

Padiolleau-Lefevre, S., C. Alexandrenne, F. Dkhissi, G. Clement, S. Essono, C. Blache, J. Y. Couraud, A. Wijkhuisen, and D. Boquet. 2007. Expression and detection strategies for an scFv fragment retaining the same high affinity than Fab and whole antibody: Implications for therapeutic use in prion diseases. *Mol. Immunol.* 44: 1888-1896

Paoli, G. C., C. Y. Chen, and J. D. Brewster. 2004. Single-chain Fv antibody with specificity for *Listeria monocytogenes*. *J. Immunol. Methods* 289: 147-155

Rader, C., D. A. Cheresh, and C. F. Barbas 3rd. 1998. A phage display approach for rapid antibody humanization: designed combinatorial V gene libraries. *Proc. Natl. Acad. Sci. U.S.A.* 95: 8910-8915)

Roggenkamp, R., Z. Janowicz, B. Stanikowski, and C. P. Hollenberg. 1984. Biosynthesis and regulation of the peroxisomal methanol oxidase from the methylotrophic yeast *Hansenula polymorpha*. *Mol. Gen. Genet.* 194: 489-493

Saini, S. S., B. Allore, R. M. Jacobs, and A. Kaushik. 1999. Exceptionally long CDR3H region with multiple cysteine residues in functional bovine IgM antibodies. *Eur. J. Immunol.* 29: 2420-2426

Saini, S. S., W. Farrugia, P. A. Ramsland, and A. K. Kaushik. 2003. Bovine IgM antibodies with exceptionally long complementarity-determining region 3 of the heavy chain share unique structural properties conferring restricted VH+Vlambda pairings. *Int. Immunol.* 15: 845-853

Schwyzer, M. and M. Ackermann. 1996. Molecular virology of ruminant herpesviruses. *Vet. Microbiol.* 53: 17-29

Silva, S. V., P. B. Little, and A. Kaushik. 1995. An immunodominant epitope on 40 kilodalton outer membrane protein is conserved among different strains of *Haemophilus* (Histophilus) somnus. *Zentralbl. Bakteriol.* 282: 449-456)

Sinclair, M. C. and R. Aitken. 1995. PCR strategies for isolation of the 5' end of an immunoglobulin-encoding bovine cDNA. *Gene* 167: 285-289.

Thiry, J., Keuser, V., Muylkens, B. et al. 2006. Vet Res. 37:169.

Tikoo S. K., Campos, M. and Babiuk, L. A. 1995. Adv. Virus Res. 45:191.

Tschopp, J. F., P. F. Brust, J. M. Cregg, C. A. Stillman, and T. R. Gingeras. 1987. Expression of the lacZ gene from two methanol-regulated promoters in *Pichia pastoris. Nucleic Acids Res.* 15: 3859-3876

Turner, D. J., M. A. Ritter, and A. J. George. 1997. Importance of the linker in expression of single-chain Fv antibody fragments: optimisation of peptide sequence using phage display technology. *J. Immunol. Methods* 205: 43-54 van Donkersgoed, J. and P. Klassen. 1995. Serological study of a modified-live virus IBR vaccine given to feedlot calves after arrival. *Can. Vet. J.* 36: 394 van Donkersgoed, J., J. V. van den Hurk, D. McCartney, and R. J. Harland. 1991. Comparative serological response in calves to eight commercial vaccines against infectious bovine rhinotracheitis, parainfluenza-3, bovine respiratory syncytial, and bovine viral diarrhea viruses. *Can. Vet. J.* 32: 727-733 van Drunen Littel-van den Hurk, S. 2006. Rationale and perspectives on the success of vaccination against bovine herpesvirus-1. *Vet. Microbiol.* 113: 275-282

Winter, G., A. D. Griffiths, R. E. Hawkins, and H. R. Hoogenboom. 1994. Making antibodies by phage display technology. *Annu. Rev. Immunol.* 12: 433-455.

Yates, W. D. 1982. A review of infectious bovine rhinotracheitis, shipping fever pneumonia and viral-bacterial synergism in respiratory disease of cattle. *Can. J. Comp. Med.* 46: 225-263

Zhang, J. L., J. J. Gou, Z. Y. Zhang, Y. X. Jing, L. Zhang, R. Guo, P. Yan, N. L. Cheng, B. Niu, and J. Xie. 2006. Screening and evaluation of human single-chain fragment variable antibody against hepatitis B virus surface antigen. *Hepatobiliary. Pancreat. Dis. Int.* 5: 237-241

The invention claimed is:

1. A single chain variable fragment (scFv) that binds and neutralizes BHV-1 virus comprising the amino acid sequence as shown in SEQ ID NO:2, 5 or 6 or a variant thereof, wherein the variations of the variant consist of conservative amino acid modifications in the linker region.

2. The scFv of claim 1, wherein the scFv is encoded by the nucleotide sequence as shown in SEQ ID NO:3, 7 or 8 or a variant thereof, wherein the variations of the variant consist of conservative substitutions in the linker region.

3. A composition comprising the scFv of claim 1 and a pharmaceutically acceptable excipient, carrier, buffer or stabilizer.

4. A method of treating BHV-1 infection in cattle comprising administering an effective amount of the scFv according to claim 1 to a cow or bull.

5. A method of neutralizing BHV-1 in cattle comprising administering an effective amount of the scFv according to claim 1 to a cow or bull.

6. A method of neutralizing BHV-1 in infected semen obtained from a bull comprising administering an effective amount of the scFv according to claim 1 to the infected semen.

7. The method according to claim 4 comprising administering BHV-1 during transportation or parturition.

8. The method according to claim 4, wherein the cattle have bovine respiratory disease or bovine genital disease.

9. The method according to claim 4, via passive immunization.

10. The method according to claim 4, wherein the scFv is administered intra-nasally.

11. The method according to claim 4, wherein the scFv is administered intravaginally.

12. The method according to claim 4, wherein the scFv is administered by injection.

13. The method according to claim 4, wherein the scFv is administered mucosally.

14. The method according to claim 4, in conjunction with conventional immunization.

15. A kit for treating or diagnosing bovine respiratory disease, bovine genital disease, or infected semen, comprising an effective amount of the scFv of claim 1 and directions for use thereof.

16. A method of detecting BHV-1 infection in a cow comprising assaying a sample from the cow for binding with an scFv according to claim 1, wherein binding by the scFv is indicative of a cow being infected with BHV-1.

17. A method of determining whether a cow is vaccinated comprising assaying a sample from the cow for binding with an scFv according to claim 1, wherein binding by the scFv is indicative of a vaccinated cow and lack of binding is indicative of an unvaccinated cow.

18. The method of claim 16 wherein assaying the sample is by an immunoassay.

19. A diagnostic agent comprising (1) a scFv that binds and neutralizes BHV-1 virus according to claim 1 attached to (2) a label that produces a detectable signal, directly or indirectly.

20. The diagnostic agent of claim 19, wherein the label is a radioisotope, a fluorescent compound, a chemiluminescent compound, an enzyme, an imaging agent or a metal ion.

21. A kit comprising the diagnostic agent of claim 19 and instructions for use thereof.

* * * * *

UNITED STATES PATENT AND TRADEMARK OFFICE
CERTIFICATE OF CORRECTION

PATENT NO. : 8,383,115 B2
APPLICATION NO. : 12/669345
DATED : February 26, 2013
INVENTOR(S) : Azad Kumar Kaushik et al.

It is certified that error appears in the above-identified patent and that said Letters Patent is hereby corrected as shown below:

In the Claims:

In claim 1 at column 41, line 34, "1D" should read "ID"; and

In claim 2 at line 41, line 38, "1D" should read "ID".

Signed and Sealed this
Twenty-third Day of July, 2013

Teresa Stanek Rea
*Acting Director of the United States Patent and Trademark Office*

SEQUENCE LISTING

```
<160> NUMBER OF SEQ ID NOS: 16

<210> SEQ ID NO 1
<211> LENGTH: 7
<212> TYPE: PRT
<213> ORGANISM: Artificial Sequence
<220> FEATURE:
<223> OTHER INFORMATION: Synthesized

<400> SEQUENCE: 1

Gly Gln Ser Ser Arg Ser Ser
1               5

<210> SEQ ID NO 2
<211> LENGTH: 242
<212> TYPE: PRT
<213> ORGANISM: Artificial Sequence
<220> FEATURE:
<223> OTHER INFORMATION: Synthesized

<400> SEQUENCE: 2

Gln Ala Val Leu Thr Gln Pro Ser Ser Val Ser Gly Ser Leu Gly Gln
1               5                   10                  15

Arg Val Ser Ile Thr Cys Ser Gly Ser Ser Ser Asn Ile Gly Arg Tyr
                20                  25                  30

Gly Val Gly Trp Tyr Gln Gln Val Pro Gly Ser Gly Leu Arg Arg Ile
            35                  40                  45

Ile Tyr Gly Ser Val Ser Arg Pro Ser Gly Val Pro Val Arg Phe Ser
    50                  55                  60

Gly Ser Lys Ser Gly Asp Thr Ala Thr Leu Thr Ile Ser Ser Leu Gln
65                  70                  75                  80

Ala Glu Asp Glu Ala Asp Tyr Phe Cys Ala Thr Ala Asp Tyr Thr Ser
                85                  90                  95

Ser Pro Val Leu Phe Gly Ser Gly Thr Thr Leu Thr Val Leu Gly Gln
                100                 105                 110

Ser Ser Arg Ser Ser Gln Val Gln Leu Arg Glu Ser Gly Pro Ser Leu
            115                 120                 125

Val Lys Pro Ser Gln Thr Leu Ser Leu Thr Cys Thr Val Ser Gly Phe
        130                 135                 140

Ser Leu Ser Gly Asn Ser Val Gly Trp Val Arg Gln Thr Pro Gly Lys
145                 150                 155                 160

Ala Leu Glu Trp Leu Gly Asn Met Asp Gly Ile Gly Thr Thr Asp Tyr
```

```
                   165                 170                 175
Asn Pro Ala Leu Lys Ser Arg Leu Ser Ile Thr Lys Asp Asn Ser Lys
            180                 185                 190

Ser Gln Val Ser Leu Ser Leu Ser Ser Val Thr Thr Glu Asp Thr Ala
        195                 200                 205

Thr Tyr Tyr Cys Ala Lys Cys Thr Gly Ala Tyr Cys Trp Arg Phe Asp
    210                 215                 220

Asp Ala Tyr Gly Tyr Asp Asp Trp Gly Gln Gly Leu Leu Val Thr Val
225                 230                 235                 240

Ser Ser

<210> SEQ ID NO 3
<211> LENGTH: 745
<212> TYPE: DNA
<213> ORGANISM: Artificial Sequence
<220> FEATURE:
<223> OTHER INFORMATION: Synthesized

<400> SEQUENCE: 3
cggcccaggc tgtgctgact cagccgtcct ccgtgtccgg ctccctgggc cagagggtct      60
ccatcacctg ctctggaagc agcagcaaca tcggtagata tggtgtgggc tggtaccaac     120
aggtcccagg atcgggcctc agaaggatca tatatggtag tgtcagtcga ccctcggggg     180
tccccgtccg attctccggc tccaagtctg gcgacacagc caccctgacc atcagctcgc     240
tccaggctga ggacgaggcg gattatttct gtgcaactgc tgactacact agtagtcctg     300
ttcttttcgg cagcgggacc acactgaccg tcctaggtca gtcctctaga tcttcccagg     360
tgcagctgcg ggagtcgggc cccagcctgg tgaagccctc acagaccctg tccctcacct     420
gcacggtctc tggattctca ttaagcggta atagtgtagg ctgggtccgc cagactccag     480
gaaaggcgct ggagtggctc ggtaacatgg atggtatagg aaccacagac tataacccag     540
ccctgaaatc ccggctcagc atcaccaagg acaactccaa agccaagtc tctctatcac     600 tgagcagcgt aacaactgag gacacggcca catactattg tgcgaagtgt actggtgctt     660
attgctggag gtttgatgac gcttatggtt atgatgactg gggccaagga ctcctggtca     720
ccgtctcctc cactagtggc caagc                                           745

<210> SEQ ID NO 4
<211> LENGTH: 18
<212> TYPE: PRT
<213> ORGANISM: Artificial Sequence
<220> FEATURE:
<223> OTHER INFORMATION: Synthesized

<400> SEQUENCE: 4

Gly Gln Ser Ser Arg Ser Ser Ser Gly Gly Ser Ser Gly Gly Gly
1               5                   10                  15

Gly Ser

<210> SEQ ID NO 5
<211> LENGTH: 253
<212> TYPE: PRT
<213> ORGANISM: Artificial Sequence
<220> FEATURE:
<223> OTHER INFORMATION: Synthesized

<400> SEQUENCE: 5

Gln Ala Val Leu Thr Gln Pro Ser Ser Val Ser Gly Ser Leu Gly Gln
1               5                   10                  15
```

```
Arg Val Ser Ile Thr Cys Ser Gly Ser Ser Asn Ile Gly Arg Tyr
            20                  25                  30

Gly Val Gly Trp Tyr Gln Gln Val Pro Gly Ser Gly Leu Arg Arg Ile
        35                  40                  45

Ile Tyr Gly Ser Val Ser Arg Pro Ser Gly Val Pro Val Arg Phe Ser
 50                      55                  60

Gly Ser Lys Ser Gly Asp Thr Ala Thr Leu Thr Ile Ser Ser Leu Gln
 65                  70                  75                  80

Ala Glu Asp Glu Ala Asp Tyr Phe Cys Ala Thr Ala Asp Tyr Thr Ser
                    85                  90                  95

Ser Pro Val Leu Phe Gly Ser Gly Thr Thr Leu Thr Val Leu Gly Gln
                100                 105                 110

Ser Ser Arg Ser Ser Ser Gly Gly Ser Ser Gly Gly Gly Gly Ser
                115                 120                 125

Gln Val Gln Leu Arg Glu Ser Gly Pro Ser Leu Val Lys Pro Ser Gln
    130                 135                 140

Thr Leu Ser Leu Thr Cys Thr Val Ser Gly Phe Ser Leu Ser Gly Asn
145                 150                 155                 160

Ser Val Gly Trp Val Arg Gln Thr Pro Gly Lys Ala Leu Glu Trp Leu
                165                 170                 175

Gly Asn Met Asp Gly Ile Gly Thr Thr Asp Tyr Asn Pro Ala Leu Lys
                180                 185                 190

Ser Arg Leu Ser Ile Thr Lys Asp Asn Ser Lys Ser Gln Val Ser Leu
            195                 200                 205

Ser Leu Ser Ser Val Thr Thr Glu Asp Thr Ala Thr Tyr Tyr Cys Ala
    210                 215                 220

Lys Cys Thr Gly Ala Tyr Cys Trp Arg Phe Asp Asp Ala Tyr Gly Tyr
225                 230                 235                 240

Asp Asp Trp Gly Gln Gly Leu Leu Val Thr Val Ser Ser
                245                 250

<210> SEQ ID NO 6
<211> LENGTH: 253
<212> TYPE: PRT
<213> ORGANISM: Artificial Sequence
<220> FEATURE:
<223> OTHER INFORMATION: Synthesized

<400> SEQUENCE: 6

Gln Ala Val Leu Thr Gln Pro Ser Ser Val Ser Gly Ser Leu Gly Gln
 1               5                  10                  15

Arg Val Ser Ile Thr Cys Ser Gly Ser Ser Asn Ile Gly Arg Tyr
            20                  25                  30

Gly Val Gly Trp Tyr Gln Gln Val Pro Gly Ser Gly Leu Arg Arg Ile
        35                  40                  45

Ile Tyr Gly Ser Val Ser Arg Pro Ser Gly Val Pro Val Arg Phe Ser
 50                      55                  60

Gly Ser Lys Ser Gly Asp Thr Ala Thr Leu Thr Ile Ser Ser Leu Gln
 65                  70                  75                  80

Ala Glu Asp Glu Ala Asp Tyr Phe Cys Ala Thr Ala Asp Tyr Thr Ser
                    85                  90                  95

Ser Pro Val Leu Phe Gly Ser Gly Thr Thr Leu Thr Val Leu Gly Gln
                100                 105                 110

Ser Ser Arg Ser Ser Gly Gly Gly Ser Ser Gly Gly Gly Gly Ser
                115                 120                 125

Gln Val Gln Leu Arg Glu Ser Gly Pro Ser Leu Val Lys Pro Ser Gln
```

```
                    130                 135                 140
Thr Leu Ser Leu Thr Cys Thr Val Ser Gly Phe Ser Leu Ser Gly Asn
145                 150                 155                 160

Ser Val Gly Trp Val Arg Gln Thr Pro Gly Lys Ala Leu Glu Trp Leu
                165                 170                 175

Gly Asn Met Asp Gly Ile Gly Thr Thr Asp Tyr Asn Pro Ala Leu Lys
            180                 185                 190

Ser Arg Leu Ser Ile Thr Lys Asp Asn Ser Lys Ser Gln Val Ser Leu
        195                 200                 205

Ser Leu Ser Ser Val Thr Thr Glu Gly Thr Ala Thr Tyr Tyr Cys Ala
210                 215                 220

Lys Cys Thr Gly Ala Tyr Cys Trp Arg Phe Asp Asp Ala Tyr Gly Tyr
225                 230                 235                 240

Asp Asp Trp Gly Gln Gly Leu Leu Val Thr Val Ser Ser
                245                 250

<210> SEQ ID NO 7
<211> LENGTH: 778
<212> TYPE: DNA
<213> ORGANISM: Artificial Sequence
<220> FEATURE:
<223> OTHER INFORMATION: Synthesized

<400> SEQUENCE: 7
cggcccaggc tgtgctgact cagccgtcct ccgtgtccgg ctccctgggc cagagggtct    60
ccatcacctg ctctggaagc agcagcaaca tcggtagata tggtgtgggc tggtaccaac   120
aggtcccagg atcgggcctc agaaggatca tatatggtag tgtcagtcga ccctcggggg   180
tccccgtccg attctccggc tccaagtctg gcgacacagc caccctgacc atcagctcgc   240
tccaggctga ggacgaggcg gattatttct gtgcaactgc tgactacact agtagtcctg   300
ttcttttcgg cagcgggacc acactgaccg tcctaggtca gtcctctaga tcttccagcg   360
gtggtggcag ctccggtggt ggcggttccc aggtgcagct gcgggagtcg ggccccagcc   420
tggtgaagcc ctcacagacc ctgtccctca cctgcacggt ctctggattc tcattaagcg   480
gtaatagtgt aggctgggtc cgccagactc aggaaaaggc gctggagtgg ctcggtaaca   540
tggatggtat aggaaccaca gactataacc cagccctgaa atcccggctc agcatcacca   600
aggacaactc caaaagccaa gtctctctat cactgagcag cgtaacaact gaggacacgg   660
ccacatacta ttgtgcgaag tgtactggtg cttattgctg gaggtttgat gacgcttatg   720
gttatgatga ctggggccaa ggactcctgg tcaccgtctc ctcactagt ggccaagc     778

<210> SEQ ID NO 8
<211> LENGTH: 778
<212> TYPE: DNA
<213> ORGANISM: Artificial Sequence
<220> FEATURE:
<223> OTHER INFORMATION: Synthesized

<400> SEQUENCE: 8
cggcccaggc tgtgctgact cagccgtcct ccgtgtccgg ctccctgggc cagagggtct    60
ccatcacctg ctctggaagc agcagcaaca tcggtagata tggtgtgggc tggtaccaac   120
aggtcccagg atcgggcctc agaaggatca tatatggtag tgtcagtcga ccctcggggg   180
tccccgtccg attctccggc tccaagtctg gcgacacagc caccctgacc atcagctcgc   240
tccaggctga ggacgaggcg gattatttct gtgcaactgc tgactacact agtagtcctg   300
ttcttttcgg cagcgggacc acactgaccg tcctaggtca gtcctctaga tcttccggcg   360
```

```
gtggtggcag ctccggtggt ggcggttccc aggtgcagct gcgggagtcg ggccccagcc    420
tggtgaagcc ctcacagacc ctgtccctca cctgcacggt ctctggattc tcattaagcg    480
gtaatagtgt aggctgggtc cgccagactc caggaaaggc gctggagtgg ctcggtaaca    540
tggatggtat aggaaccaca gactataacc cagccctgaa atcccggctc agcatcacca    600
aggacaactc caaaagccaa gtctctctat cactgagcag cgtaacaact gagggcacgg    660
ccacatacta ttgtgcgaag tgtactggtg cttattgctg gaggtttgat gacgcttatg    720
gttatgatga ctggggccaa ggactcctgg tcaccgtctc ctccactagt ggccaagc     778
```

<210> SEQ ID NO 9
<211> LENGTH: 35
<212> TYPE: DNA
<213> ORGANISM: Artificial Sequence
<220> FEATURE:
<223> OTHER INFORMATION: Synthesized

<400> SEQUENCE: 9

```
ggtcagtcct ctagatcttc ccaggtgcag ctgcg                                35
```

<210> SEQ ID NO 10
<211> LENGTH: 39
<212> TYPE: DNA
<213> ORGANISM: Artificial Sequence
<220> FEATURE:
<223> OTHER INFORMATION: Synthesized

<400> SEQUENCE: 10

```
ctggccggct tggccactag tggaggagac ggtgaccag                            39
```

<210> SEQ ID NO 11
<211> LENGTH: 33
<212> TYPE: DNA
<213> ORGANISM: Artificial Sequence
<220> FEATURE:
<223> OTHER INFORMATION: Synthesized

<400> SEQUENCE: 11

```
gtggcccagc cggcccaggc tgtgctgact cag                                  33
```

<210> SEQ ID NO 12
<211> LENGTH: 39
<212> TYPE: DNA
<213> ORGANISM: Artificial Sequence
<220> FEATURE:
<223> OTHER INFORMATION: Synthesized

<400> SEQUENCE: 12

```
ggaagatcta gaggactgac ctaggacggt cagtgtggt                            39
```

<210> SEQ ID NO 13
<211> LENGTH: 68
<212> TYPE: DNA
<213> ORGANISM: Artificial Sequence
<220> FEATURE:
<223> OTHER INFORMATION: Synthesized

<400> SEQUENCE: 13

```
ggtcagtcct ctagatcttc cggcggtggt ggcagctccg gtggtggcgg ttcccaggtg    60
cagctgcg                                                              68
```

<210> SEQ ID NO 14
<211> LENGTH: 39

```
<212> TYPE: DNA
<213> ORGANISM: Artificial Sequence
<220> FEATURE:
<223> OTHER INFORMATION: Synthesized

<400> SEQUENCE: 14
ctggccggct tggccactag tggaggagac ggtgaccag                              39

<210> SEQ ID NO 15
<211> LENGTH: 33
<212> TYPE: DNA
<213> ORGANISM: Artificial Sequence
<220> FEATURE:
<223> OTHER INFORMATION: Synthesized

<400> SEQUENCE: 15
gtggcccagc cggcccaggc tgtgctgact cag                                   33

<210> SEQ ID NO 16
<211> LENGTH: 39
<212> TYPE: DNA
<213> ORGANISM: Artificial Sequence
<220> FEATURE:
<223> OTHER INFORMATION: Synthesized

<400> SEQUENCE: 16
ggaagatcta gaggactgac ctaggacggt cagtgtggt                              39
```